US008715181B2

(12) United States Patent
Brynelsen et al.

(10) Patent No.: US 8,715,181 B2
(45) Date of Patent: May 6, 2014

(54) FEEDBACK SYSTEMS AND METHODS FOR COMMUNICATING DIAGNOSTIC AND/OR TREATMENT SIGNALS TO ENHANCE OBESITY TREATMENTS

(75) Inventors: Charles R. Brynelsen, Menlo Park, CA (US); Mace Volzing, Campbell, CA (US); Rose Province, San Jose, CA (US); Mike Hedman, Saratoga, CA (US); Matthew Hills, Los Altos, CA (US)

(73) Assignee: IntraPace, Inc., Mountain View, CA (US)

( * ) Notice: Subject to any disclaimer, the term of this patent is extended or adjusted under 35 U.S.C. 154(b) by 0 days.

(21) Appl. No.: 13/457,961

(22) Filed: Apr. 27, 2012

(65) Prior Publication Data

US 2012/0214140 A1    Aug. 23, 2012

Related U.S. Application Data

(63) Continuation of application No. 12/754,435, filed on Apr. 5, 2010, now abandoned.

(60) Provisional application No. 61/166,636, filed on Apr. 3, 2009.

(51) Int. Cl.
*A61B 5/00* (2006.01)
*G06F 19/00* (2011.01)

(52) U.S. Cl.
CPC ............... *G06F 19/34* (2013.01); *A61B 5/6871* (2013.01)
USPC ........................................................ 600/301

(58) Field of Classification Search
USPC ................................................ 600/300–301
See application file for complete search history.

(56) References Cited

U.S. PATENT DOCUMENTS 3,411,507 A    4/1964   Wingrove
3,646,940 A    3/1972   Timm et al.
(Continued)

FOREIGN PATENT DOCUMENTS

EP    0 129 483        12/1984
EP    0 864 293 A1     9/1998
(Continued)

OTHER PUBLICATIONS

Bellahsene, et al., "Evaluation of a Portable Gastric Stimulator," Ninth Annual Conference of the Engineering in Medicine and Biology Society, 2 pages total. (1987).

(Continued)

*Primary Examiner* — Bill Thomson
*Assistant Examiner* — Bobby Soriano
(74) *Attorney, Agent, or Firm* — Kilpatrick Townsend & Stockton LLP

(57) ABSTRACT

Feedback systems and methods communicate implanted sensor-based feedback signals to promote behavior modifications that ameliorate obesity and other eating disorders. The system and methods described may also be applicable to any treatment in which presenting feedback regarding patients' eating and exercise habits is desired. The present invention provides a method and system for treating a patient by collecting ingestion and exercise information about the patient from an implanted sensor and communicating the collected information to the patient, his or her physician and/or other health care providers. In some embodiments, stimulation of the patient's stomach is also provided to reduce caloric intake. In some embodiments, the collected data is transmitted to a central server. Further embodiments may provide access to additional information in conjunction with the collected patient information, such as a calorie database, an exercise planner, and so forth, with the data optionally being used within a social networking system.

7 Claims, 12 Drawing Sheets

(56) References Cited

U.S. PATENT DOCUMENTS

| | | |
|---|---|---|
| 3,662,758 A | 5/1972 | Glover |
| 3,677,251 A | 7/1972 | Bowers |
| 3,735,766 A | 5/1973 | Bowers et al. |
| 3,796,221 A | 3/1974 | Hagfors |
| 3,815,611 A | 6/1974 | Denniston, III |
| 3,835,865 A | 9/1974 | Bowers |
| 4,102,344 A | 7/1978 | Conway |
| 4,592,339 A | 6/1986 | Kuzmak et al. |
| 4,628,928 A | 12/1986 | Lowell |
| 4,823,808 A | 4/1989 | Clegg |
| 4,921,481 A | 5/1990 | Danis et al. |
| 4,925,446 A | 5/1990 | Garay |
| 4,966,148 A | 10/1990 | Millar |
| 5,112,310 A | 5/1992 | Grobe |
| 5,188,104 A | 2/1993 | Wernicke et al. |
| 5,193,540 A | 3/1993 | Schulman et al. |
| 5,197,491 A | 3/1993 | Anderson et al. |
| 5,217,449 A | 6/1993 | Yuda et al. |
| 5,263,480 A | 11/1993 | Wernicke et al. |
| 5,292,344 A | 3/1994 | Douglas |
| 5,415,181 A | 5/1995 | Hogrefe et al. |
| 5,423,872 A | 6/1995 | Cigaina |
| 5,438,985 A | 8/1995 | Essen-Moller |
| 5,540,730 A | 7/1996 | Terry et al. |
| 5,558,640 A | 9/1996 | Pfeiler et al. |
| 5,626,630 A | 5/1997 | Markowitz et al. |
| 5,690,691 A | 11/1997 | Chen et al. |
| 5,716,392 A | 2/1998 | Bourgeois et al. |
| 5,767,791 A | 6/1998 | Stoop et al. |
| 5,792,048 A | 8/1998 | Schaefer |
| 5,800,445 A | 9/1998 | Ratcliff |
| 5,836,994 A | 11/1998 | Bourgeois |
| 5,861,014 A | 1/1999 | Familoni |
| 5,865,843 A | 2/1999 | Baudino |
| 5,928,195 A | 7/1999 | Malamud et al. |
| 5,938,669 A | 8/1999 | Klaiber et al. |
| 5,980,480 A | 11/1999 | Rubenstein et al. |
| 5,993,473 A | 11/1999 | Chan et al. |
| 5,995,872 A | 11/1999 | Bourgeois |
| 6,026,326 A | 2/2000 | Bardy |
| 6,041,258 A | 3/2000 | Cigaina et al. |
| 6,083,249 A | 7/2000 | Familoni |
| 6,091,992 A | 7/2000 | Bourgeois et al. |
| 6,097,984 A | 8/2000 | Douglas |
| 6,098,629 A | 8/2000 | Johnson et al. |
| 6,104,955 A | 8/2000 | Bourgeois |
| 6,115,635 A | 9/2000 | Bourgeois |
| 6,150,951 A | 11/2000 | Olejniczak |
| 6,205,359 B1 | 3/2001 | Boveja |
| 6,214,032 B1 | 4/2001 | Loeb et al. |
| 6,216,039 B1 | 4/2001 | Bourgeois |
| 6,243,607 B1 | 6/2001 | Mintchev et al. |
| 6,285,897 B1 | 9/2001 | Kilcoyne et al. |
| 6,317,731 B1 | 11/2001 | Luciano |
| 6,321,124 B1 | 11/2001 | Cigaina |
| 6,327,503 B1 | 12/2001 | Familoni |
| 6,366,814 B1 | 4/2002 | Boveja et al. |
| 6,381,495 B1 | 4/2002 | Jenkins |
| 6,381,577 B1 | 4/2002 | Brown |
| 6,427,089 B1 | 7/2002 | Knowlton |
| 6,449,511 B1 | 9/2002 | Mintchev et al. |
| 6,453,199 B1 | 9/2002 | Kobozev |
| 6,454,785 B2 | 9/2002 | De Hoyos Garza |
| 6,477,423 B1 | 11/2002 | Jenkins |
| 6,510,332 B1 | 1/2003 | Greenstein |
| 6,513,532 B2 * | 2/2003 | Mault et al. ............... 600/595 |
| 6,529,778 B2 | 3/2003 | Prutchi |
| 6,533,733 B1 | 3/2003 | Ericson et al. |
| 6,535,764 B2 | 3/2003 | Imran et al. |
| 6,540,789 B1 | 4/2003 | Silverman et al. |
| 6,542,776 B1 | 4/2003 | Gordon et al. |
| 6,564,101 B1 | 5/2003 | Zikria |
| 6,571,127 B1 | 5/2003 | Ben-Haim et al. |
| 6,572,629 B2 | 6/2003 | Kalloo et al. |
| 6,591,137 B1 | 7/2003 | Fischeli et al. |
| 6,600,953 B2 | 7/2003 | Flesler et al. |
| 6,606,518 B1 | 8/2003 | Cigaina |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,684,104 B2 | 1/2004 | Gordon et al. |
| 6,689,056 B1 | 2/2004 | Kilcoyne et al. |
| 6,731,976 B2 | 5/2004 | Penn et al. |
| 6,754,536 B2 | 6/2004 | Swoyer et al. |
| 6,778,854 B2 | 8/2004 | Puskas |
| 6,826,428 B1 | 11/2004 | Chen et al. |
| 6,879,859 B1 | 4/2005 | Boveja |
| 6,879,970 B2 | 4/2005 | Shiffman et al. |
| 6,895,278 B1 | 5/2005 | Gordon |
| 6,895,279 B2 | 5/2005 | Loeb et al. |
| 6,941,171 B2 | 9/2005 | Mann et al. |
| 7,016,735 B2 | 3/2006 | Imran et al. |
| 7,020,526 B1 | 3/2006 | Zhao |
| 7,020,531 B1 | 3/2006 | Colliou et al. |
| 7,033,373 B2 | 4/2006 | de la Torre et al. |
| 7,044,942 B2 | 5/2006 | Jolly et al. |
| 7,054,692 B1 | 5/2006 | Whitehurst et al. |
| 7,076,305 B2 | 7/2006 | Imran et al. |
| 7,096,070 B1 | 8/2006 | Jenkins et al. |
| 7,107,100 B2 | 9/2006 | Imran et al. |
| 7,120,498 B2 | 10/2006 | Imran et al. |
| 7,371,215 B2 | 5/2008 | Colliou et al. |
| 7,399,304 B2 | 7/2008 | Gambale et al. |
| 7,463,934 B2 | 12/2008 | Tronnes et al. |
| 7,502,649 B2 | 3/2009 | Ben-Haim et al. |
| 7,530,943 B2 | 5/2009 | Lechner |
| 7,558,629 B2 | 7/2009 | Keimel et al. |
| 7,590,452 B2 | 9/2009 | Imran et al. |
| 7,702,394 B2 | 4/2010 | Imran |
| 2001/0011543 A1 | 8/2001 | Forsell |
| 2001/0049470 A1 * | 12/2001 | Mault et al. ............... 600/300 |
| 2002/0055757 A1 | 5/2002 | de la Torre et al. |
| 2002/0072780 A1 | 6/2002 | Foley |
| 2002/0103521 A1 | 8/2002 | Swoyer et al. |
| 2002/0103522 A1 | 8/2002 | Swoyer et al. |
| 2002/0161414 A1 | 10/2002 | Flesler et al. |
| 2002/0198570 A1 | 12/2002 | Puskas |
| 2003/0055463 A1 | 3/2003 | Gordon et al. |
| 2003/0120328 A1 | 6/2003 | Jenkins et al. |
| 2003/0144708 A1 | 7/2003 | Starkebaum |
| 2003/0167025 A1 | 9/2003 | Imran et al. |
| 2003/0212439 A1 | 11/2003 | Schuler et al. |
| 2004/0015201 A1 | 1/2004 | Greenstein |
| 2004/0059393 A1 | 3/2004 | Policker et al. |
| 2004/0088022 A1 | 5/2004 | Chen |
| 2004/0093039 A1 | 5/2004 | Schumert |
| 2004/0133089 A1 | 7/2004 | Kilcoyne et al. |
| 2004/0147816 A1 | 7/2004 | Policker et al. |
| 2004/0162595 A1 | 8/2004 | Foley |
| 2004/0162945 A1 | 8/2004 | King et al. |
| 2004/0167583 A1 | 8/2004 | Knudson et al. |
| 2004/0172084 A1 | 9/2004 | Knudson et al. |
| 2004/0172086 A1 | 9/2004 | Knudson et al. |
| 2004/0172088 A1 | 9/2004 | Knudson et al. |
| 2004/0172095 A1 | 9/2004 | Jenkins et al. |
| 2004/0176812 A1 | 9/2004 | Knudson et al. |
| 2004/0236381 A1 | 11/2004 | Dinsmoor et al. |
| 2004/0236382 A1 | 11/2004 | Dinsmoor et al. |
| 2004/0243195 A1 | 12/2004 | Imran et al. |
| 2005/0021101 A1 | 1/2005 | Chen et al. |
| 2005/0038454 A1 | 2/2005 | Loshakove |
| 2005/0049655 A1 | 3/2005 | Boveja et al. |
| 2005/0055039 A1 | 3/2005 | Burnett et al. |
| 2005/0065571 A1 | 3/2005 | Imran |
| 2005/0096514 A1 | 5/2005 | Starkebaum |
| 2005/0113880 A1 | 5/2005 | Gordon |
| 2005/0131486 A1 | 6/2005 | Boveja et al. |
| 2005/0131487 A1 | 6/2005 | Boveja et al. |
| 2005/0137643 A1 | 6/2005 | Mintchev |
| 2005/0143760 A1 | 6/2005 | Imran |
| 2005/0143784 A1 | 6/2005 | Imran |
| 2005/0149141 A1 | 7/2005 | Starkebaum |
| 2005/0149142 A1 | 7/2005 | Starkebaum |

(56) References Cited

U.S. PATENT DOCUMENTS

| | | |
|---|---|---|
| 2005/0149146 A1 | 7/2005 | Boveja et al. |
| 2005/0159800 A1 | 7/2005 | Marshall et al. |
| 2005/0159801 A1 | 7/2005 | Marshall et al. |
| 2005/0192599 A1 | 9/2005 | Demarais |
| 2005/0222637 A1 | 10/2005 | Chen |
| 2005/0222638 A1 | 10/2005 | Foley et al. |
| 2005/0251219 A1 | 11/2005 | Evans |
| 2005/0287499 A1* | 12/2005 | Yeager .................... 434/127 |
| 2006/0020298 A1 | 1/2006 | Camilleri et al. |
| 2006/0025654 A1 | 2/2006 | Suzuki et al. |
| 2006/0036293 A1 | 2/2006 | Whitehurst et al. |
| 2006/0058851 A1 | 3/2006 | Cigaina |
| 2006/0069414 A1 | 3/2006 | Imran et al. |
| 2006/0074279 A1* | 4/2006 | Brover .................... 600/300 |
| 2006/0074335 A1 | 4/2006 | Ben-Oren et al. |
| 2006/0074457 A1 | 4/2006 | Imran et al. |
| 2006/0074458 A1 | 4/2006 | Imran |
| 2006/0085054 A1 | 4/2006 | Zikorus et al. |
| 2006/0089571 A1 | 4/2006 | Gertner |
| 2006/0089699 A1 | 4/2006 | Imran |
| 2006/0111753 A1 | 5/2006 | Imran et al. |
| 2006/0116735 A1 | 6/2006 | Imran et al. |
| 2006/0116736 A1 | 6/2006 | DiLorenzo |
| 2006/0122864 A1* | 6/2006 | Gottesman et al. ............ 705/2 |
| 2006/0173238 A1 | 8/2006 | Starkebaum |
| 2006/0212053 A1 | 9/2006 | Gertner |
| 2006/0224326 A1 | 10/2006 | St. Ores et al. |
| 2006/0293609 A1 | 12/2006 | Stahmann et al. |
| 2007/0179359 A1* | 8/2007 | Goodwin .................. 600/300 |
| 2007/0299481 A1 | 12/2007 | Syed et al. |
| 2008/0161875 A1 | 7/2008 | Stone |
| 2008/0208010 A1 | 8/2008 | Boyden et al. |
| 2009/0012433 A1* | 1/2009 | Fernstrom et al. ............ 600/593 |
| 2009/0030474 A1 | 1/2009 | Brynelsen et al. |
| 2009/0054914 A1 | 2/2009 | Lechner |
| 2009/0192404 A1 | 7/2009 | Ortiz et al. |
| 2009/0222057 A1 | 9/2009 | Imran |
| 2009/0299434 A1 | 12/2009 | Imran et al. |
| 2009/0306462 A1 | 12/2009 | Lechner |
| 2010/0152532 A1 | 6/2010 | Marcotte |
| 2010/0217213 A1 | 8/2010 | Forsell |
| 2010/0234693 A1* | 9/2010 | Srinivasan et al. ............ 600/300 |
| 2010/0240962 A1* | 9/2010 | Contant .................... 600/300 |
| 2011/0034760 A1 | 2/2011 | Brynelsen et al. |
| 2011/0087076 A1 | 4/2011 | Brynelsen et al. |
| 2012/0190955 A1* | 7/2012 | Rao et al. .................. 600/368 |

FOREIGN PATENT DOCUMENTS

| | | |
|---|---|---|
| EP | 0 571 938 | 4/1999 |
| WO | 98/43700 | 10/1998 |
| WO | 98/53878 | 12/1998 |
| WO | 00/30534 | 6/2000 |
| WO | 01/58389 | 8/2001 |
| WO | 01/76690 | 10/2001 |
| WO | 2006/083885 A1 | 8/2006 |
| WO | 2008/063486 A2 | 5/2008 |
| WO | 2008/117296 A1 | 10/2008 |
| WO | 2008/139463 A2 | 11/2008 |
| WO | 2009/048380 A1 | 4/2009 |
| WO | 2009/048386 A1 | 4/2009 |

OTHER PUBLICATIONS

Cigaina et al., "Gastric Myo-Electrical Pacing As Therapy for Morbid Obesity: Preliminary Results," Obes Surg;9:333-334, (1999).

Daniel et al., "Electrical Activity of the Gastrointestinal Tract as an Indication of Mechanical Activity," Am. J. of Digestive Diseases, 8(1):54-102, (1963).

Eagon et al., "Effects of Gastric Pacing on Canine Gastric Motility and Emptying," The American Physiological Society, 265(4):G767-G774, (Oct. 1993).

Eagon et al., "Gastrointestinal Pacing, Surgical Clinics of North America," 73(6): 1161-1172 (Dec. 1993).

Electric Stimulation of the Gastrointestinal Tract, GP, p. 151 (Apr. 1964).

Familoni, "Efficacy of Electrical Stimulation at Frequencies Higher Than Basal Rate in Canine Stomach," Digestive Diseases and Sciences, 42(5):892-897, (May 1997).

Familoni, et al., "Electrical Pacing of the Stomach in Dogs, Engineering in Medicine and Biology Society," IEEE Proceedings of the Annual International Conference, 6:2315-2316 (Oct. 29-Nov. 1, 1992).

Geldof et al., "Electrogastrographic Study of Gastric Myoelectrical Activity in Patients With Unexplained Nausea and Vomiting," Gut, 27:799808, (1986).

Hocking, "Postoperative Gastroparesis and TachygastriaResponse to Electric Stimulation and Erythromycin," Surgery, 114(3):538-542 (Sep. 1993).

Joshi et al., "Anesthesia for Laparoscopic Surgery," Canadian Journal of Anesthesia 49(6):R1-R5 (2002).

Kelly et al., "Role of the Gastric Pacesetter Potential Defined by Dectrical Pacing," Canadian J. of Physiology and Pharmacology, 50:1017-1019, (1972).

Kelly, Differential Responses of the Canine Gastric Corpus and Antrum to Electric Stimulation, Am. J. of Physiology. 226(1):230-234, (Jan. 1974).

Kelly, et al., "Pacing the Canine Stomach With Electric Stimulation," Am. J. of Physiology, 222(3):588-594 (Mar. 1972).

Kubota, et al., "Manometric Evaluation of Children With Chronic Constipation Using a Suction-Stimulating Electrode," Eur. J. Pediari. Surg. 2:287-290, (1992).

Miedema et al., "Pacing the Human Stomach," Surgery, 143-150, (Feb. 1992).

Sarna et al., "Electrical Stimulation of Gastric Electrical Control Activity," Am. 1. of Physiology, 225(1):125-131, (Jul. 1973).

Sarna, et al., "Gastric Pacemakers," Gastroenterology. 70:226-231, (1976).

Swain, et al., "An Endoscopically Deliverable Tissue-Transfixing Device for Securing Biosensors in The Gastrointestinal Tract," Gastrointestinal Endoscopy, 40(6):730-734 (1994).

U.S. Appl. No. 10/109,296; first named inventor: Mir A. Imran; filed Mar. 26, 2002.

U.S. Appl. No. 12/637,452, filed Dec. 14, 2009; first named inventor: Matthew Hills.

U.S. Appl. No. 12/754,439, filed Apr. 5, 2010; first named inventor: Charles R. Brynelsen.

U.S. Appl. No. 61/241,154, filed Sep. 10, 2009; first named inventor: Rose Province.

International Search Report and Written Opinion of PCT Application No. PCT/US2010/029969, mailed Jul. 28, 2010, 10 pages total.

International Preliminary Report on Patentability of PCT Application No. PCT/US2010/029969, dated Oct. 4, 2011, 7 pages.

Hughes, et al., "Balance (Bioengineering Approaches for Lifestyle Activity and Nutrition Continuous Engagement): Developing New Technology for Monitoring Energy Balance in Real Time," Journal of Diabetes Science and Technology, vol. 4, Issue 2, Mar. 2010, pp. 429-434.

* cited by examiner

FEEDBACK SYSTEMS AND METHODS FOR COMMUNICATING DIAGNOSTIC AND/OR TREATMENT SIGNALS TO ENHANCE OBESITY TREATMENTS

CROSS-REFERENCE TO RELATED APPLICATIONS

This application is a continuation application of U.S. patent application Ser. No. 12/754,435, filed Apr. 5, 2010, which claims the benefit under 35 USC 119(e) of U.S. Provisional Application No. 61/166,636, filed Apr. 3, 2009; the full disclosure of which is incorporated herein by reference in its entirety.

The subject matter of the present application is also related to the following applications: U.S. application Ser. No. 12/145,430 filed Jun. 24, 2008, U.S. application Ser. No. 10/950,345, filed Sep. 23, 2004 (Allowed), and U.S. Application No. 61/122,315, filed Dec. 12, 2008; all of which are herein incorporated by reference in their entirety.

BACKGROUND OF THE INVENTION

Since the mid-seventies, the prevalence of obesity has increased sharply for both adults and children. These increasing rates raise concern because of their implications for Americans' health. Being overweight or obese may increase the risk of many diseases and health conditions, including: hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (such as endometrial, breast, and colon).

Obesity and its associated health problems have a significant economic impact on the U.S. health care system. Medical costs associated with excess weight and obesity may involve direct and indirect costs. Direct medical costs may include preventive, diagnostic, and treatment services related to obesity. Indirect costs relate to morbidity and mortality costs. Morbidity costs are defined as the value of income lost from decreased productivity, restricted activity, absenteeism, and bed days. Mortality costs are the value of future income lost by premature death.

Many therapies are currently being investigated for treatment of obesity and diseases associated with obesity. To date, the widely used obesity treatments have not been shown to be ideal, particularly for those afflicted with severe obesity. The approaches that have been proposed range from lifestyle coaching to major surgical therapies. Unfortunately, patient compliance and the accuracy with which patients report their own activities can significantly limit the effectiveness of coaching and support groups. While surgical approaches can limit the capacity of the patient's food intake over a set amount of time regardless of compliance, quite severe surgical modifications may have to be imposed to achieve the desired result. Notwithstanding that, as a group, obese patients may be highly motivated to find a solution to help them lose weight and to improve their health, obese individuals will often exhibit behavior which circumvents or limits the efficacy of therapies so that effective surgical approaches may have to significantly restrict gastrointestinal function, while more moderate approaches may not achieve the desired results. Nonetheless, improved awareness of obesity's role in increasing the incidence of other serious health issues is contributing to overweight consumers' desire to take a more active role in the management of their weight, lifestyle and health.

Therefore, it would be desirable to provide devices, systems and methods that can effectively promote behavior modification of patients suffering from obesity and other eating disorders. It would also be desirable to provide services that would help increase a patient's perception of satiety and reduce caloric intake. It would also be desirable to provide improved assessment of a patient's actual behavior. Ideally, such a system would provide a patient, his or her physician, a lifestyle coach, support group, and/or other caregivers access to the information collected about the patient's eating and exercise habits for use in monitoring the patient's progress and so as to present actual behavior-based information to the patient for effective behavior modification and greater success in achieving weight loss or health goals.

BRIEF SUMMARY OF THE INVENTION

The present invention relates to feedback systems and methods for modifying volitional behavior by a patient, in exemplary embodiments by communicating diagnostic and/or treatment signals to enhance obesity treatments. Although embodiments of the invention make specific reference to treatment for obesity, the system and methods described herein may be applicable to other treatments seeking patient behavior modification, and particularly eating disorders and other disorders in which presenting feedback regarding patients' actual eating and/or exercise habits is desired. Embodiments of the present invention provide a method and system for treating a patient by collecting ingestion and exercise information about the patient from an implanted sensor and presenting the sensor-based information to the patient, his or her physician, members of a support group, and/or other health care providers. The presentation of the information may include graphically or verbally communicating the information to the patient using an automated graphical or audio output, and/or the information can be communicated to a health coach such as a physician, lifestyle coach, or other support group member who then communicates to the patient. Hence, the sensor-based information can provide accurate and reliable behavior-modification feedback to the patient. In some embodiments, stimulation of the patient's stomach is also provided to reduce caloric intake, with or without presentation of information regarding that stimulation to the patient. In some embodiments, the collected data is transmitted to a central server or centralized data collection mechanism via a telecommunication system. Further embodiments may provide access to additional information in conjunction with the collected patient information, such as a calorie database, an exercise planner, and so forth. In many embodiments, implanted sensor-based information may be accessed via a server by any member of a group having an appropriate permission granted by the patient in which the sensor is implanted. Hence, exemplary systems may employ aspects of social networking to enhance the efficacy of the feedback provided to a patient, thereby taking advantage of the relationships within the network to improve the health of the patient.

In a first aspect, embodiments of the present invention provide a method of treating a patient. The method includes implanting a device in the body of the patient, where the implanted device includes at least one sensor. Patient data is collected with the sensor(s) in response to ingestion by the patient and in response to activity by the patient. The patient data is analyzed to determine ingestion and activity information about the patient, and the ingestion and activity information is presented so as to promote healthy behavior by the patient.

The ingestion and activity information will typically comprise eating and exercise information, respectively. Along with the eating and exercise information, drinking information and sleep information may also be provided through the analysis of the patient data. In some embodiments, the eating and exercise information is presented graphically and/or verbally by a data processing system to a data system user, who may be the patient or a health coach of the patient. Remote access to the information may also be provided, optionally via the internet or another telecommunication system.

In some embodiments, the step of presenting the eating and exercise information includes presenting a graphical display of the information.

In some embodiments, the step of presenting the eating and exercise information includes displaying the information via a website. The method may also include accepting self-reported data input to the website by the patient (often per a prompt generated in response to signals from the sensor), analyzing the patient input data in conjunction with the sensor patient data, and presenting the analysis to a user.

In some embodiments, the implanted device includes stimulation circuitry for providing therapeutic stimulation to the patient. The stimulation may optionally be applied to tissues of the patient without presenting stimulation information and/or otherwise communicating to the patient regarding the stimulation. Alternative embodiments may include presenting stimulation information along with the other information presented to the patient.

In some embodiments, the eating and exercise information is provided to at least one of the patient, a physician of the patient, a nutritionist of the patient, a member of a support group to which the patient belongs, or another health coach of the patient so as to facilitate feedback to the patient regarding his or her actual eating and exercise behavior to help modify the actual behavior toward a healthy behavior.

In a second aspect, embodiments of the present invention provide a system for providing feedback to treat a patient. The system includes an implantable sensor adapted to be coupled to the stomach of the patient; a wireless transmitter coupled to the sensor; a home monitor comprising a processor, a storage medium, and transmitting/receiving circuitry. A remote server is also provided, and the home monitor is in communication with the sensor and the server via the transmitting/receiving circuitry and is configured to receive patient sensor-based food ingestion and/or activity data from the sensor and transmit the patient data to the server.

In some embodiments, the wireless transmitter transmits sensor data to the home monitor when the patient is within a proximal distance of the home monitor. The proximal distance may be less than about 30 feet or less than about 20 feet, so that the telemetry between the patient and the home monitor may be effective at a range of from 0 to 30 feet.

In some embodiments, the server or centralized data collection mechanism comprises a tangible medium embodying machine-readable instructions for analyzing the patient data received from the home monitor and for communicating analysis results to the patient or another user. The server may be configured to communicate the analysis results to the user via at least one of an email, a text message, a phone call, or a web page. The analysis results may include healthy behavior goal success rates.

In some embodiments, the system also includes patient stimulation circuitry that is wirelessly coupled to the home monitor, where the circuitry is adapted to be implanted in the patient. The patient stimulation control may optionally be remotely reprogrammed using the telemetry between the home monitor and the implanted device, and using internet connectivity of the home monitor (or an associated computer).

In some embodiments, the home monitor is also configured to receive data from at least one of an electronic scale, a glucose monitor, a telephone, an image capture device, or a personal digital assistant. The home monitor may optionally comprise or be incorporated into a personal computer, a smart phone, or the like.

In a third aspect, embodiments of the present invention provide a method of communicating patient diagnostic and treatment information. The method includes obtaining sensor data from at least one sensor implanted in a patient, where the sensor data is collected by the sensor(s) at intervals over a period of time. The sensor data is presented to a user via a graphical interface so as to promote sensor-based behavior modification of the patient.

In some embodiments, the method includes accepting patient-input data and presenting the patient-input data along with the sensor data. The method may further include comparing the patient-input data with the sensor data and presenting comparison information to the user.

In some embodiments, the sensor data includes ingestion information and/or activity-level information.

In some embodiments, the graphical interface is configured to allow the user to customize the presentation of the sensor data.

In some embodiments, the graphical interface is configured to display at least one of a calorie database, a calorie counter, a packaged food database, meal preparation support, an activity diary, an exercise guide and planner, a weight tracking log, a body-mass index calculator, activity reports, meal frequency and duration reports, and a message center.

In some embodiments, the graphical interface may be a secure website. The website may be configured to allow the user to input information.

In a fourth aspect, embodiments of the present invention provide a system for treating a patient. The system includes an implantable device that has at least one sensor where the device is configured to collect patient data with the sensor(s) in response to ingestion by the patient and in response to exercise by the patient when the device is implanted in a patient body. The system also includes a processor that may be coupled to the implantable device so as to, in response to the patient data, analyze the patient data to determine sensor-based ingestion information and sensor-based exercise information about the patient. The system further includes a user interface coupled to the processor that communicates the sensor-based eating and exercise information so as to provide behavior modifying feedback to the patient.

In yet another aspect, the invention provides a method of treating an eating disorder of a patient. The method comprises implanting a sensor in a body of the patient. A group is identified using permission obtained from the patient to add members to the group. Information that is generated using sensor signals from the sensor is uploaded to a server, with the information corresponding to sensed ingestion and/or exercise of the patient. In response to permission data regarding the group, message data is transmitted from the server or centralized data collection mechanism to a device associated with a member of the group. The message data is generated using the uploaded information. A message is presented to the member in response to the message data. The message is configured to promote the member interacting with the patient, and specifically so as to encourage healthy behavior by the patient.

In many embodiments, the patient will be prompted, in response to sensor signals from the sensor, to enter at least a portion of the information. The prompt may be delivered via a device associated with the patient, with the patient entering the information into the device so that the information can be uploaded to the server or centralized data collection mechanism. For example, the device may comprise a personal computer or smart phone, and the device may inform the patient that the sensor has indicated an eating event has taken place. The prompt may request that the patient specify one or more servings that have been ingested, including their content, size, and so forth. Alternatively, the prompt may indicate that the patient has had a heightened activity level and requesting that the patient specify any exercise performed.

In many embodiments, the message will comprise a positive reinforcement message so as to promote the member of the group contacting the patient to encourage a continuation of health-benefiting behavior by the patient. The server or centralized data collection mechanism may, for example, transmit message data that generates such a positive reinforcement message in response to the sensor indicating that eating events have been limited to those associated with an ingestion goal, such as eating only at appropriate meal times. Positive reinforcement messages may also be initiated in response to exercise activity meeting or exceeding an exercise goal. Some positive reinforcement messages may be generated in response to a quantitative measurement of the patient indicating that a weight related goal has been achieved. For example, the patient may have undergone a change in weight of at least 5 kilograms, or the patient may have maintained a desired weight for a desired amount of time. As changes in weight may appear a relatively long time after initiation of improvements in life style, alternative quantitative measurements may include a change in a size measurement of the patient (such as a reduction in a dress size, a circumference of the waist, arms, or legs, a change in an exercise performance, or the like. Preferably, the message will be transmitted to the group member within two days of events sensed by the sensor, or of the quantitative measurement. Transmission of the message may optionally be much more immediate, such as within a day of the sensed event, within an hour of the sensed event, within fifteen minutes of the event, in near-real time, or the like.

In other embodiments, the message may comprise a negative reinforcement message seeking to have a member of the group discourage unhealthy behavior by the patient. The server or centralized data collection mechanism will typically transmit this negative reinforcement message data in response to and within two days of eating events sensed by the sensor exceeding an ingestion goal, and/or within two days of exercise activity sensed by the sensor being below an exercise goal. Transmission of the negative reinforcement messages may again be much more immediate, such as within a day of the sensed event, within an hour of the sensed event, within fifteen minutes of the event, in near-real time, or the like. Alternative messages may be sent that are time based instead of being based on triggered events. As an example a reminder message may be transmitted at the end of the work week with suggested activities and menu items for the weekend, or an inspirational message could be sent each day.

In many embodiments, the patient will belong to a support group of patients having implanted sensors. In such embodiments, additional messages may be transmitted to the patient regarding the sensed data from another member of the group. For example, in an obesity support group in which more than one member has an implant that can sense ingestion and/or exercise, one member having an implant may receive messages regarding sensed data from an implant of another member. This allows the support group members to encourage each other toward healthy behavior, and to discourage each other away from excessive eating, failure to meet exercise goals, or the like.

In many embodiments, the message will comprise information about ingestion, and may identify sensor-based eating events of the patient. The message may comprise information about exercise, and may identify sensor-based exercise activities of the patient.

In many embodiments, an ingestion and/or exercise goal may be generated in response to input from the patient. The goal may be compared to eating information and/or exercise information so as to generate comparison data. The comparison data may be transmitted to a member of the group so as to encourage the member to help increase alignment between the behavior of the patient and the goals. This may involve modifying the behavior of the patient, and/or modifying the near term, interim, or long term goals of the patient toward a more achievable level. Hence, interactive goal development may be promoted within the group. Group or team goals may also be developed, with the team including multiple weight loss members of the group. Messages may also include input from (and/or be sent in response to input from) a physician or other healthcare provider.

In another aspect, the invention provides a method for treating an eating disorder of the patient. The patient has an implanted sensor, and the method includes receiving uploaded information regarding ingestion and/or exercise of the patient with a server or centralized data collection mechanism. The information is generated using sensor signals from the sensor. In response to permission data, message data is transmitted from the server or centralized data collection mechanism to a device associated with a member of a group. The group is identified using permission obtained from the patient. The message data is generated using the information and is configured so as to induce the device to present a message to the member of the group. The message promotes the member providing encouragement for the patient, with the encouragement urging the patient toward healthy behavior.

In another aspect, the invention provides a system for treating an eating disorder of a patient. An implantable sensor generates sensor signals in response to eating events, and/or in response to exercise activity of the patient when the sensor is implanted. A server or centralized data collection mechanism is coupleable to the sensor and to a patient device, typically via a home monitor, a handheld device such as a smart phone or personal digital assistant, or the like. The server or centralized data collection mechanism is configured to transmit message data to a device associated with a member of a group. The patient inputs permission allowing members to be added to the group, and message data is generated in response to the sensor signals. The message is transmitted per the permission. The message data induces the device associated with the member of the group to present a message to that member. The message is configured to promote the member urging healthy eating and/or exercise behavior by the patient.

In yet another aspect, the invention provides a system for treating a plurality of patients. Each patient has an associated device and an implanted sensor generating sensor signals. The system comprises a server or centralized data collection mechanism coupleable to the sensors and the patient devices. The server or centralized data collection mechanism is configured to transmit message data to the device associated with a first patient, the message data being generated in response to the sensor signals from a second patient. Optionally, the server or centralized data collection mechanism may similarly transmit additional message data to the device associated with the second patient, with the additional message data being generated in response to the sensor signals from the first patient.

BRIEF DESCRIPTION OF THE DRAWINGS

FIG. 8 is a screen shot showing dashboard information and functions from which a patient can grant, modify, or remove permission of a member of a support group to receive information based on a sensor implanted in the patient, as well as providing access to communication with other group members, messages regarding sensor-based information from other group members, and the like.

DETAILED DESCRIPTION OF THE INVENTION

Figure 1:
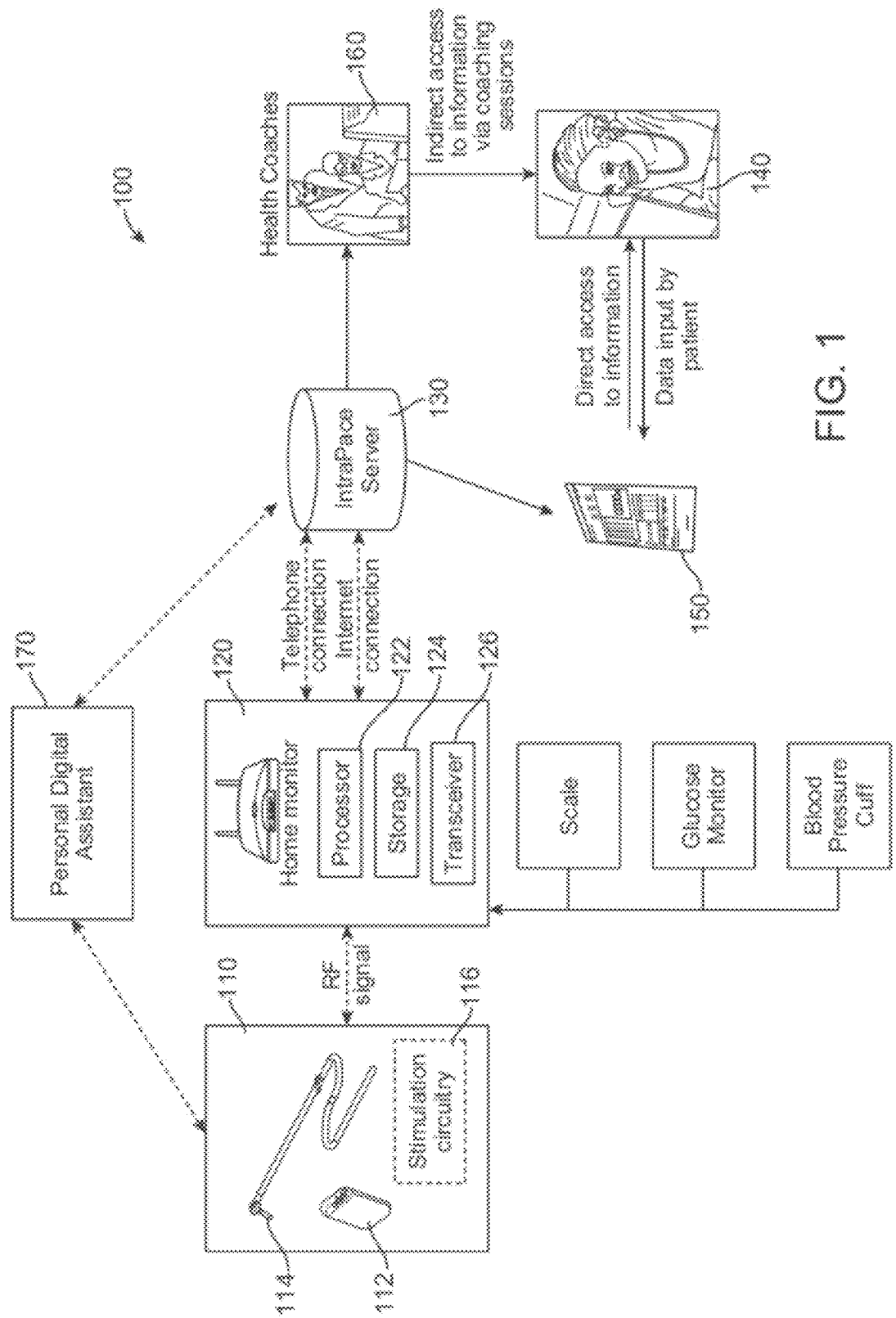
FIG. 1 illustrates an embodiment of a treatment system of the present invention.

The present invention relates to feedback systems and methods for communicating implanted sensor-based information so as to affect behavior modification for eating disorders. Although embodiments of the invention make specific reference to a treatment for obesity, the system and methods described herein may be applicable to any treatment in which presenting feedback regarding patients' eating and/or exercise habits is desired.

Embodiments of the present invention collect information regarding the patient's eating and exercise habits via one or more sensors implanted within the body of the patient or one or more sensors externally coupled or attached to the patient's body. This information can then be reviewed by a clinician during office visits and used in coaching the patient. Coaching may include helping the patient to make healthy lifestyle choices, such as specifically encouraging the patient to decrease his or her caloric intake while increasing his or her caloric expenditure and receiving adequate, good-quality sleep, since indirectly sleep influences a patient's desire to eat and the manner in which the ingested food is metabolized. Compliance with physician advice may be low in obese patients and caloric intake is often under-reported while caloric expenditures are often over-reported. Although eventually weight gain or loss by a patient will indicate the accuracy of the patient's reporting, the objective monitoring systems provided herein will significantly improve many patients' ability to acknowledge their actual behavior, to identify elements of their behavior that can be changed to improve health, and to effect incremental changes toward achieving long term health goals. While scales are lagging indicators of actions that lead to weight loss or gain, the present invention includes leading indicators of actions that lead to weight loss or gain. The advantage of a leading indicator is that a person, e.g. a patient, can adjust to data changes as they are occurring; this will likely result in a better weight loss outcome than with a lagging indicator. The systems and methods described herein may identify eating and other behaviors which the patient is not aware of (including night-time eating and the like). These systems and methods may also improve the correlation between positive patient behavior and beneficial positive reinforcement, and decrease deleterious correlations between negative patient behavior (such as under-reporting of actual ingestion, over-reporting activity levels, and the like) with misguided positive reinforcement. Such improvements may be particularly effective at promoting and/or maintaining healthy activities when ultimate health goals remain distant.

The sensor and feedback system of the present invention is not subject to the reporting bias of the patient, thus presenting an objective view. In addition, embodiments of the present invention allow data to be collected twenty-four hours per day, seven days per week, which provides an accurate record of the patient's behavior without dependence upon the patient's memory or commitment to the eating and exercise tracking process. Some embodiments may sense and/or restrict caloric intake, such as using a band implanted around the stomach so as to constrict flow along the gastrointestinal tract, a gastric balloon inflated within the stomach, any other ingestion restricting device, or the like.

In still other embodiments, the present invention also provides stimulation of the stomach to reduce caloric intake.

Embodiments of the invention provide a system that accesses the data collected by the implanted system remotely. The system is then accessible by the patients and/or the patients' health coaches to support the patient in achieving their weight reduction goals. The automated availability of behavior modification feedback, shortened time between "coaching sessions" and increased accuracy of the sensor data will improve outcomes for the patients.

In some embodiments, the invention may employ aspects of social networking systems, with sensor-based information that has been generated using signals from an implanted sensor often being available to one or more members of a group. The group may, at least in part, be defined by the patient giving permission to particular individuals. Other members of the group (such as the patient and a supervising physician) may be defined when the group is first organized. Many patients having implanted sensors may join a mutual support group of patients, with sensor-based data being shared between the implant recipients. Advantageously, these systems may allow patients to receive feedback within a relatively short time after exhibiting behavior that is sensed by the sensor, preferably within two days of the sensor identifying an eating event or activity level, and ideally within one day of the behavior. Using telemetry-based communication between the implanted device and a home monitor (or other intermediate device), some embodiments may allow daily uploads, and/or send messages to a smart phone or personal digital assistant (PDA) in near real time, so as to support the patient at a time of need when eating, to help the patient avoid self-defeating behaviors when they are likely to take place as well as reinforce the beneficial behaviors when they occur. This significant shortening of the time delay between patient behavior and relationship-based feedback to the patient may provide significant advantages over feedback provided through monthly, quarterly, or annual appointments with a dietician or physician. Nonetheless, communication enhancement described herein may provide increased efficacy for alternative embodiments that rely on uploading of patient data during such routine appointments.

To facilitate the relationships employed for implant patient feedback, embodiments of the invention may make use of aspects of Web-2.0 systems such as FaceBook™ social networking systems and methods, MySpace™ social networking systems and methods, Linked In™ social networking systems and methods, or the like. Embodiments may also employ aspects of known weight reduction support group systems and methods, particularly those that are enhanced through electronic telecommunications such as the WeightWatchers.com™ weight management portal, TheDailyPlate.com™ nutrition and weight management system, and the like. The sensor data sharing aspects of many embodiments may employ systems somewhat analogous to (and/or may be modified from) web-enabled athletic training community systems such as those of TrainingPeaks.com™ and EnduranceNation.us™. Still further aspects of the invention may be facilitated by systems and methods that have been developed (and are continuing to be developed, and/or will be developed in the future) in support of Health 2.0 concepts. Hence, embodiments of the inventions described herein may leverage or be modified from a variety of known technologies, including by employing Elgg tools and solutions for creation of online communities as available at http://elgg.org.

An example system 100 suitable for implementation of embodiments of the present invention is illustrated in FIG. 1. In the embodiment shown, the system 100 comprises an implanted device or assembly 110 that communicates with a home monitor 120 via a wireless transmitter disposed in an implant housing 112, such as an RF telemetry module. The implanted device 110 includes at least one sensor 114, a processor (not shown) and, optionally, stimulation circuitry 116 (typically disposed in-part in housing 112, and ideally also including an electrode disposed along a lead body coupling sensor 114 to housing 112) for providing therapeutic stimulation to the patient. A server or centralized data collection mechanism 130 communicates with home monitor 120 via an internet or other telecommunication system so as to allow access to sensor-based data via a portal 150 and/or health coach workstation 160, thereby providing sensor-based feedback to a patient 140 (through direct presentation of the sensor-based information to the patient, and/or through a health-coach/patient relationship).

Each of implanted device 110, home monitor 120, server 130, health coach workstation 160, and a portable patient device will typically include associated data processing systems, with the overall feedback system 100 combining their data manipulation and communication capabilities into an overall data architecture. Generally, the data processing systems included in the discreet devices of the invention may include at least one processor. For implantable device 110, this will typically include circuitry implanted in the patient. Other devices of system 100 will include circuitry external of the patient. Such external processor circuitry may include one or more proprietary processor boards, and/or may make use of a general purpose desktop computer, notebook computer, handheld computer, smart phone, or the like. The external processor may communicate with a number of peripheral devices (and/or other processors) and these peripheral devices may include a data and/or programming storage subsystem or memory. The peripheral devices may also include one or more user interface input devices, user interface output devices, and a network interface subsystem to provide an interface with other processing systems and networks such as the Internet, an intranet, and/or the like. Feedback system 100 may interface with a WII Fit™ gaming Device, Garmin or Polar watches, external heart rate monitors or calorie counters, such as Bodybugg from BodyMedia, as well as digital scales, blood pressure cuffs, etc. Implanted circuitry of the processor system may have some of the constituent components described above for the external circuitry as well being coupled to an implanted battery or other power source, with the implanted circuitry generally employing processors, data and software storage, and wireless communication capabilities (although hard-wired embodiments or other transcutaneous data transmission techniques could also be employed). Optionally, known or proprietary rechargeable implantable power sources may be used.

Both external and implanted memory of the devices of system 100 will often be used to store, in a tangible storage media, machine readable instructions or programming in the form of a computer executable code embodying one or more of the methods described herein. The memory may also similarly store data for implementing one or more of these methods. The memory may, for example, include a random access memory (RAM) for storage of instructions and data during program execution, and/or a read only memory (ROM) in which fixed instructions are stored. Persistent (non-volatile) storage may be provided, and/or the memory may include a hard disk drive, a compact digital read only memory (CD-ROM) drive, an optical drive, DVD, CD-R, CD-RW, fixed or removable flash memory, memory sticks, solid-state removable memory, and/or other fixed or removable media cartridges or disks. Some or all of the stored programming code may be altered after implantation and/or initial use of the device to alter functionality of the system.

The functions and methods described herein may be implemented with a wide variety of hardware, software, firmware, and/or the like. In many embodiments, the various functions will be implemented by modules, with each module comprising data processing hardware and associated software configured to perform the desired function. The modules may be largely integrated together so that a single processor board runs a single integrated code for each device, but will often be separated so that, for example, more than one processor board or chip or a series of subroutines or codes are used. Similarly, a single functional module may be separated into separate subroutines or be run in part on separate processor chip that is integrated with another module. Hence, a wide variety of centralized or distributed data processing architectures and/or program code architectures may be employed within different embodiments.

The electronic circuitry of the various devices of system 100 communicates via RF wired or wireless networking, and/or via telecommunications linkages for coordinating the presentation of sensor-based feedback from implanted device 110 to patient 140, as well as to monitor and facilitate the various operations of the devices, including sensing, stimulating, signal transmission, charging and/or using energy from a battery device for powering the various devices, and the like. In some embodiments, the electronic circuitry of one or more of the devices includes an internal clock. The internal clock may also include a real time clock component. The internal clock and/or real time clock may be used to control stimulation, e.g., by stimulating or allowing stimulation at a particular time of the day. The real time clock component may also provide a date/time stamp for detected events that are stored as information in a memory device, including sensor-based events, patient presentation events (such as accessing portal 150, receiving a text message, communicating with a health coach or group member, or the like). Optionally, the memory may be preserved by saving information corresponding to an event of interest which is saved along with the time/date when the event occurred.

Sensor 114 is coupled to the stomach so as to generate signals responsive to ingestion, with the sensor ideally comprising at least one temperature sensor for sensing temperature information from within the stomach. The sensors may be located on or extend from housing 112 of implanted device 110 and/or the sensors may be located on or extend from a lead or other device. Alternatively or additionally, a sensor may be located separately on the stomach wall and/or a sensor may be otherwise positioned elsewhere within, coupled to or in communication with the patient. In some embodiments, data obtained from the sensor may be pre-processed to remove noise or unwanted artifacts before it is analyzed. Additional sensors may be included, including an accelerometer and/or a heart rate sensor to measure patient activity or the like. The housing of implanted device 110 will typically contain a battery and circuitry of the implanted device, and may be similar to other known implantable stimulator housing structures used for heart pacemaker systems and the like. A suitable heart rate sensor may comprise an electrode or other sensor engaging the stomach wall so as to receive far field electric signals from the heart. Optionally, such a heart rate sensor may employ the same electrode as used to stimulate stomach tissue to inhibit ingestion, though separate electrodes may alternatively be used. Heart signals, accelerometer signals, and/or other activity sensor signals may, like temperature or other ingestion sensor signals, be recorded and processed using circuitry 116 and a processor 122. Suitable sensors and implantable devices, as well as aspects of the other devices of the devices of system 100, are described in (and/or may be modified from those described in) U.S. patent application Ser. No. 12/145,430, filed on Jun. 24, 2008 and U.S. patent application Ser. No. 10/950,345, filed on Sep. 23, 2004, both of which have previously been herein incorporated by reference. Processing of sensor signals so as to identify or classify ingestions events and/or patient activity level to be communicated by system 100 (which may occur partially or entirely in implanted device 110, home monitor 120, or server or centralized data collection mechanism 130) may be more fully understood with reference to Provisional U.S. Patent Application No. 61/122,315, filed on Dec. 12, 2008 and U.S. patent application Ser. No. 12/637,452, filed on Dec. 14, 2009 which were also previously incorporated herein by reference. Still further approaches for processing implant-generated signals so as to identify and/or classify ingestion events are described in U.S. application Ser. No. 12/754,439, filed concurrently herewith and entitled "Feedback Systems and Methods to Enhance Obstructive and Other Obesity Treatments," the disclosure of which is also incorporated herein by reference.

The home monitor 120 includes processor 122, a storage medium 124, and transmitting/receiving circuitry 126 and is capable of interrogating the implanted system 110 (and of receiving sensor-based data in response) when the patient is within a predetermined distance of the monitor. In some embodiments, this distance is approximately twenty to thirty feet. The data interrogation could also be initiated by the patient via an input into home monitor 120 or a mobile device such as an iPhone® smart phone with Abiliti™ mobile device software. The information communicated to the home monitor 120 is encrypted and sent via the internet to a Health Insurance Portability and Accountability Act (HIPPA) and European Union privacy laws compliant server or centralized data collection mechanism 130. The information is then accessible directly by the patient 140 or by approved medical personnel serving as the patient's health coaches (optionally via a workstation 160) via a secure web site or other portal 150. While the home monitor will often comprise a desktop computer or other desktop unit powered by a wall plug, alternative systems may employ home monitors with smaller form factors (the home monitor optionally comprising and/or being similar in size to a notebook computer, a smart phone, a personal digital assistant, or the like) powered by batteries or other portable power sources. Where wireless phone capability is not available to a patient (such as for a patient visiting or living in a rural area) the home monitoring system could also comprise a hand held computer and a port that is connected to the internet via a land-based telecommunications link such as via a modem and telephone connection. The implanted device could be interrogated through radiofrequency (RF) communication with the handheld computer. Such a handheld computer could also be used to enter journal information. Placing the hand-held computer in the port would allow uploading of retrieved device data, and journal entries to the internet portal. Some or all of the functionality of the home monitor 120 may instead be implemented using a portable device 170 such as a smart phone, personal digital assistant, or the like. Even when a home monitor 120 is included in the system, such portable devices will allow the patient to benefit from communications to and/or from server 130 when the patient is out of the house.

The server 130 contains software embodying a number of algorithms that evaluate the implanted device data logs in comparison with goals established by the patient and his or her health coaches 160. Based upon the results of the analysis, such as whether the goals have been met, coaching messages may be sent to the patient and support team for example via email, text message or telephone call. In alternative embodiments, audio, tactile, and/or tissue stimulation feedback may also be sent using downloadable ringtones emitted by an audio speaker in the device or communicating wirelessly with a Bluetooth device in the patient's ear, vibrations of the implanted device or of a wireless communication device external to the patient, such as miniature earplugs inserted in the patient's ears, electrical stimulation of either a diaphragm to cause hiccup, or a small electrical buzz from a device housing that stimulates tissue in a device pocket and alerts the patient.

The messages are designed to provide encouragement for positive results and positive reminders for negative or neutral results. This coaching feature encourages patients to obtain energy balance in their lives. Specific examples regarding energy expenditure include sending encouraging messages for meeting daily or weekly activity goals or sending patient alerts if extended periods of sedentary activity have occurred. With regard to caloric intake, examples include communicating feedback to the patient as to whether eating patterns show adherence to the eating plan or whether caloric intake is meeting daily, weekly, or monthly goals.

In alternative embodiments, feedback to patients may be administered in the form of an escrow account where, if the patient meets the required goals, a certain sum of money is donated to a charity favored by the patient, and if the patient fails to reach the goals, the sum of money is donated to a cause or charity that the patient despises. In another alternative embodiment, at least a portion of the feedback to patients is transmitted via benefits and/or liabilities within a virtual game, such as a virtual game character who, for example, can be depicted as thriving if the patient reaches his goals, but becomes sickly and may die if the patient fails to reach his goals; in yet another embodiment, the virtual game character "talks" to the patient about his caloric input versus caloric output. The social networking aspect of system 100 will be open to other software developers to adapt other games or technologies that can be added to the system 100. For example, patients utilizing a GPS watch could choose to upload their activity to the social networking web site, providing recognition of their accomplishment and encouragement for other patients.

Information in the data logs from the activity and consumption sensors of the implanted device 110 will also allow cross-checking between the patient's activity and meal diary and device-detected events. If the diaried and the detected events do not match (such as when the sensed data indicates that food was ingested but a snack or meal was not logged in the diary, or when a meal time or food intake quantity exceeds a logged meal), then reminders may be sent to the patient to enter additional information in the diaries, and/or to a health coach to check in with the patient. Diary entries may be made by a patient via multiple devices (for example, using a home computer when at home, a notebook computer when at the office or traveling, and/or a Smart Phone while at a restaurant, or the like) and in a variety of different formats (including options for text diary entries, voice entries, photo entries taken via a digital camera or telephone, and the like). Although diaries for the purpose of calorie counting have been typically inaccurate due to lack of patient compliance or attention, this feedback system facilitates improved accuracy. In addition, alerts can be set that send performance summary reports to the patient's health coach and/or physician, which allows the health coach or physician to intervene when needed. The intervention could be in the form of extra coaching for the patient, revising of a weight loss/exercise plan, reprogramming of the implanted device stimulation parameters, or the like.

In embodiments of the present invention, the patient may be provided with a hand-held or pocket device capable of receiving reminders and other notices from the server or centralized data collection mechanism 130, or the reminders may be sent to a general purpose hand-held or pocket device such as a cell phone or e-mailer, optionally using an appropriate local user interface or other software resident on that device. A patient identification and/or password may optionally be entered into the portable device to obtain patient data so as to prevent others from accessing sensor-based data. The notices transmitted to the portable device may include daily inspirational messages; diet and exercise education information; and particularly feedback messages (for example, identifying positive and negative events, reached daily goals, missed goals, mealtime reminders, skipped meals, excessive meal quantities or times, and/or added meals or snacks). The feedback messages may be generated by algorithms contained on the server 130; and/or cross-checking between device data logs and patient reporting. In one alternative, the portable device will include a help or 911-style button that is part of the Abiliti™ mobile device. The portable device will send a text or email message to the patient's support group in response to activation of the button. Such a button may be used when the patient determines that they need immediate support (for example, when they are feeling down or are about to make a negative lifestyle choice). The server will immediately send back a series of system generated messages designed to support the patient until a support group member or a friend can contact them.

People tend to migrate towards the normative behavior of the group. In the case of obese patients, if they surround themselves with healthy persons, they are more likely to adopt their (healthy) behaviors. Thus persons may be included into the network that have positive behaviors to leverage this. For example, these persons may include allied health professionals or patients that have been successful in changing their lifestyle and can serve as leaders to the next wave of patients coming through. In some embodiments of the invention, patients may be offered the option to join an online support group of patients with similar body mass indexes (BMI) who have similar attributes and weight loss goals. This group may meet online using the website 150 to provide support for one another, as well as review each other's results and provide support and encouragement to each other via email or text messaging via their patient-associated portable devices. Hence, the patients may optionally share access to their sensor-based data with one or more other appropriate patients so as to allow the other patients to act as health coaches to the patient in which device 110 was implanted, and/or so as to allow the implant patient to coach those other patients based on their associated sensor-based data. The patient will also optionally have the ability to invite health coaches into the online community, with the patient typically granting and managing a support group of the patient by granting permission to individuals to whom the patient is willing to allow access to the patient's sensor-based data. The supporter or member of the group may be a spouse, a gym coach, a parent, a friend, or a family member. In some embodiments, the group may include another patient having an implant providing sensor-based data. Hence, the group may comprise a mutual support group.

The patient and/or health coach may obtain updates by accessing a web site or other portal 150. The portal will optionally comprise a secure website into which the patient or other system user enters a patient identifier and/or password, allowing patients to log into the site with confidence that the system is safe and secure. Patients should feel sensitive medical data is sufficiently protected and that highly sensitive medical data is not displayed as appropriate given the value of the portal. Portal 150 may optionally comprise a "support dashboard," includes a comprehensive set of weight loss tools designed to support the individual. In addition, the support dashboard may allow access to the data logged by the implanted device 110 by the patient. The usefulness of the weight loss tools included in portal 150 may be enhanced through the ease by which the patient is provided accurate information on his or her daily activity and consumption. The sensor-based information may optionally be enhanced by patient reporting of specific food quantities, food types, caloric intake, and/or the like. The support dashboard may include features such as: a calorie database, an online calorie counter, a packaged food database, meal preparation support (such as custom meal menus generated for that patient), an activity diary, an exercise guide and planner, a weight tracking log, a body-mass index calculator, activity or exercise reports, meal frequency and duration reports, and/or a message center. Additionally, the support dashboard may allow registered dietitians and exercise physiologists who are part of the patient support group to provide guidance on healthy menu options to maintain a low calorie diet, exercise regimens compatible with the patients' weight and physical capabilities. This type of additional support may be offered through a combination of automated or system generated data and real person generated data. Portal 150 may present patient performance based on predetermined activity and caloric goals, optionally including daily kilocalories to be burned, daily calories consumed, and/or a net summary of the patient's energy balance. Portal 150 may also present additional sensor-based data, including sleep or rest data (such as the number of hours slept, a quantified quality of sleep or other rest periods, and the like).

Referring still to FIG. 1, portal 150 may have a food calculator to look up calories of food types, to input quantities of their planned or consumed meals, and the like. Food calories can be input and/or determined in a variety of different ways, with the site optionally employing a food calculator or linking to a commercial calorie identifying website such as CalorieKing.com or the like. Meal logging may optionally include uploading data or photos to the portal directly or by linking to a meal logging web-base service such as that which was offered commercially by myfoodphone.com. Thus, a photo of a meal on a plate may be analyzed by an outside expert to determine the type of food and likely caloric content. Alternatively, the photo of a meal may serve as a reminder to the patient to enter the composition of the meal and use caloric calculators to determine the caloric value of the meal. In another alternative, artificial intelligence is used to identify the components and the caloric value of the meal. Meal logging may also be performed verbally. For example, a patient may call a phone number from a cellular phone and record a message regarding the composition of the meal. The message may be transcribed and the transcript may be sent to the patient in an e-mail, or the meal composition information may be entered directly into a database set up for the patient. In another alternative, upon detection of an eating event, interactive voice recognition (IVR) may be used to call, text, SMS text, or send a pre-recorded message to patients for information regarding the caloric content of the ingested meal.

Portal 150 may also have commercially available look-up caloric and/or nutritional data from food suppliers, including commercial prepackaged customized foods suppliers, restaurant chains, or the like, supplying caloric content of the food choices being served. Patients will be able to access the database for assistance in their choices or the database may be used to send healthy choice suggestions, as part of a smart phone application. The caloric content of food may also be entered by entering a product's UPC bar code into a caloric content data base that link a product's UPC bar code to caloric value information.

Portal 150 may facilitate networking with identified friends using known social networking capabilities, giving users the ability to message friends and health care providers and accept input from such individuals so as to allow them to make public or private comments and the like. The members may connect into a live chat room sponsored by the health care practitioner support group (if desired). This may allow real time coaching based on an individual's own performance on eating, exercise and lifestyle opportunities. The portal may also support a group or circle of friends to allow individuals to chat real time or transmit messages to one another. Portal 150 may optionally accept predetermined or customized user data, allowing the user to store desired health related information on their personal page, and to control the access of others to that information. This data could include blood pressure, glucose and other data indicative of the general health status or goals of the patient. The portal will allow for daily notes from the individual, this will allow users to note overall feelings of wellness or questions they might have about eating and motivations.

To enhance the efficacy of coaching and overall feedback, portal 150 may allow for feedback from the network based on the individual's goals. The site will allow for messaging to the individuals own page (as well as other portable or connected device, as described above) which the user chooses. This messaging may be configured to prompt the individual based on performance achieved or notes about missed activity events, meal events, etc. The portal may also notify users when a member of their selected member friends has achieved their personal goals and/or accomplishments. Portal 150 may also include goal-setting and behavior/goal comparison tools. Simple goal setting fields may optionally be available for the patient, though more sophisticated systems may allow the patient to enter a long-term goal and may interactively help the patient to determine short term and long term intermediary goals so as to reach their ultimate weight reduction target. The system may, for example, provide an indication of the quantity of exercise that would be appropriate to achieve an interim or short term weight loss given the patient's sensed ingestion behavior. Alternatively, a reduction in ingestion may be determined based on maintaining the patient's sensed activity level may be identified by the system. Expected results from changes in ingestion and activity may be identified by the system. As significant weight loss may not be measured until a patient has maintained compliance for a relatively extended period, more immediate short-term goals may also be identified by the system, including reduction in a size of the patient (such as a reduction in dress or pants size, a reduction in waist size, a reduction in neck, arm, or leg circumference, an increase in walking endurance or speed, increased time in moderate or vigorous activity, improvement in heart rate recovery after exercise (or other quantifiable exercise parameters), or the like may also be identified). Portal 150 may allow the patient to revise the short term and long term goals throughout the course of treatment, and may generate comparisons between the patient's measured and sensed performance with their goals. The system may also be capable of tracking performance against team goals, with a team comprising weight-loss patients of a group. Team goals may be generated by the team, a healthcare provider of the team, or both. As an example, a physician could create a team of patients, each patient of the team having an implanted device. The physician could then work with the team to set a team's goals. This will allow the spirit of competition to be added into the mix for changing the behavior of the individual members of the team.

In some embodiments, portal 150 may include incentives or challenges that help patients pursue activities that lead to weight loss, with options including walking clubs or a virtual breast cancer walkathon. The patient may thus participate in something that supports their favorite cause and that incorporates a behavior that helps them with achieve their weight loss goals.

Portal 150 may include or be linked to one or more reference websites or to a patient database such as HealthVault® from Microsoft®. The portal will preferably have a number of selected reference sites for members to choose from. These sites will allow users to select from a number of tools which the users may prioritize or the site may keep a current list of most frequently used sites. This allows users to refer to a particular reference site based on changing priorities and behaviors. Suitable reference sites may include information on nutrition (food selection and net calorie), food preparation, activity guidelines (walking and other exercises), Kcal Expenditure charts (including activities of daily living), and/or the like. Portal 150 will allow the user to communicate their health status to others, such as by providing the ability to send permission to view the patient's page to an MD, nutritionists, or a selected friend or group member. The patient's page on the portal will typically store a history of the patient, including their weight, wireless or other uploads by or regarding the patient, and the like. Educational links may facilitate access to nutritional information, exercise information, stress management techniques, and lifestyle coaching guides.

As indicated above, a number of additional devices may communicate with the components of system 100 shown in FIG. 1. Along with portable or handheld devices 170 (such as a BlackBerry™ wireless e-mailer, an iPod™ or other mobile music player, an iPhone™ or other mobile phone, and the like), home monitor 120 or server or centralized data collection mechanism 130 may communicate with scales (for measuring a weight of the patient or food), pedometers, and the like. In exemplary embodiments, home monitor 120 receives wireless telemetry from a scale, glucose monitor, blood pressure cuff, and/or the like.

Figure 2A:
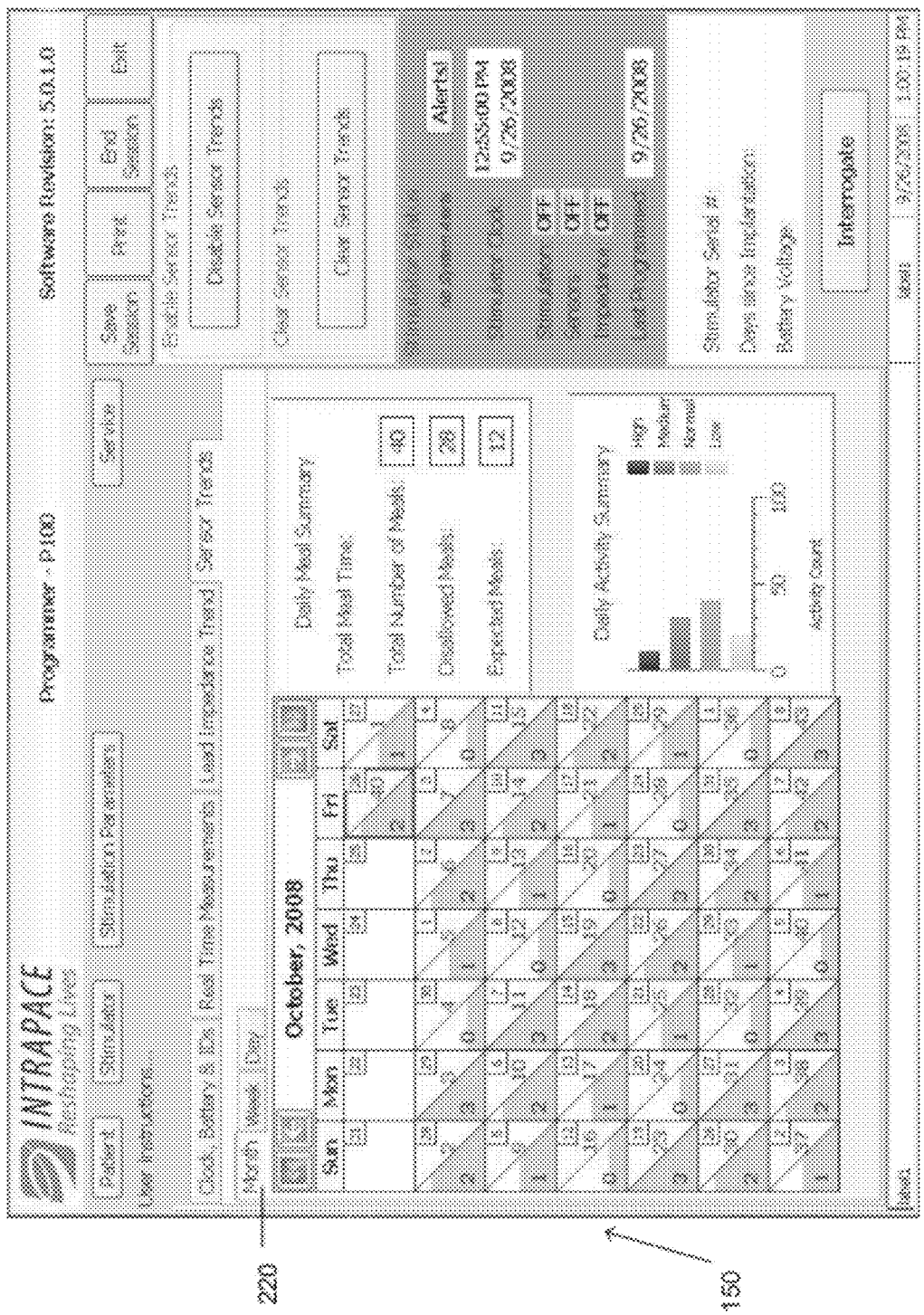
FIGS. 2A-2C show interfaces for presenting patient information according to embodiments of the present invention.
Figure 2B:
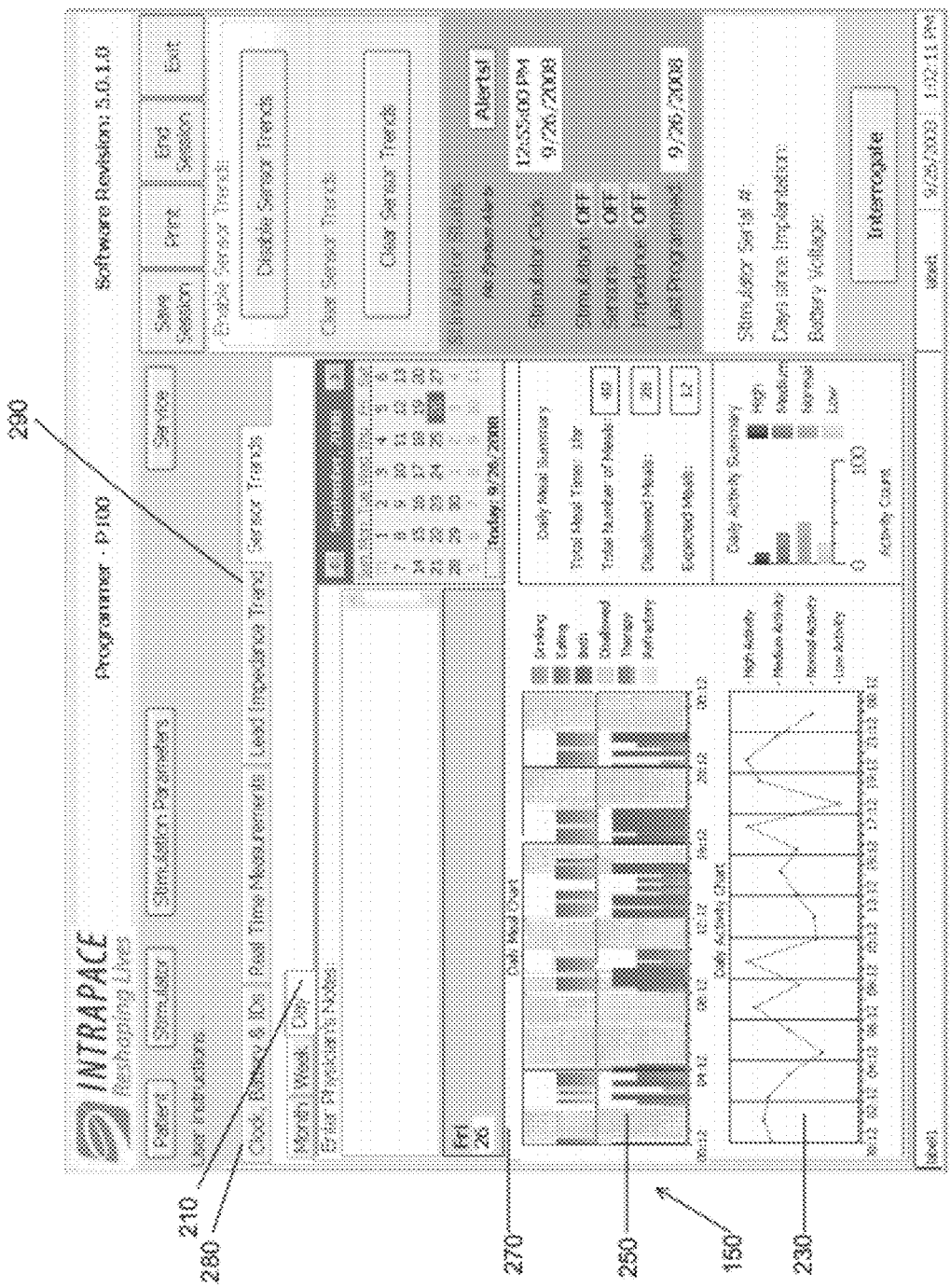
Figure 2C:
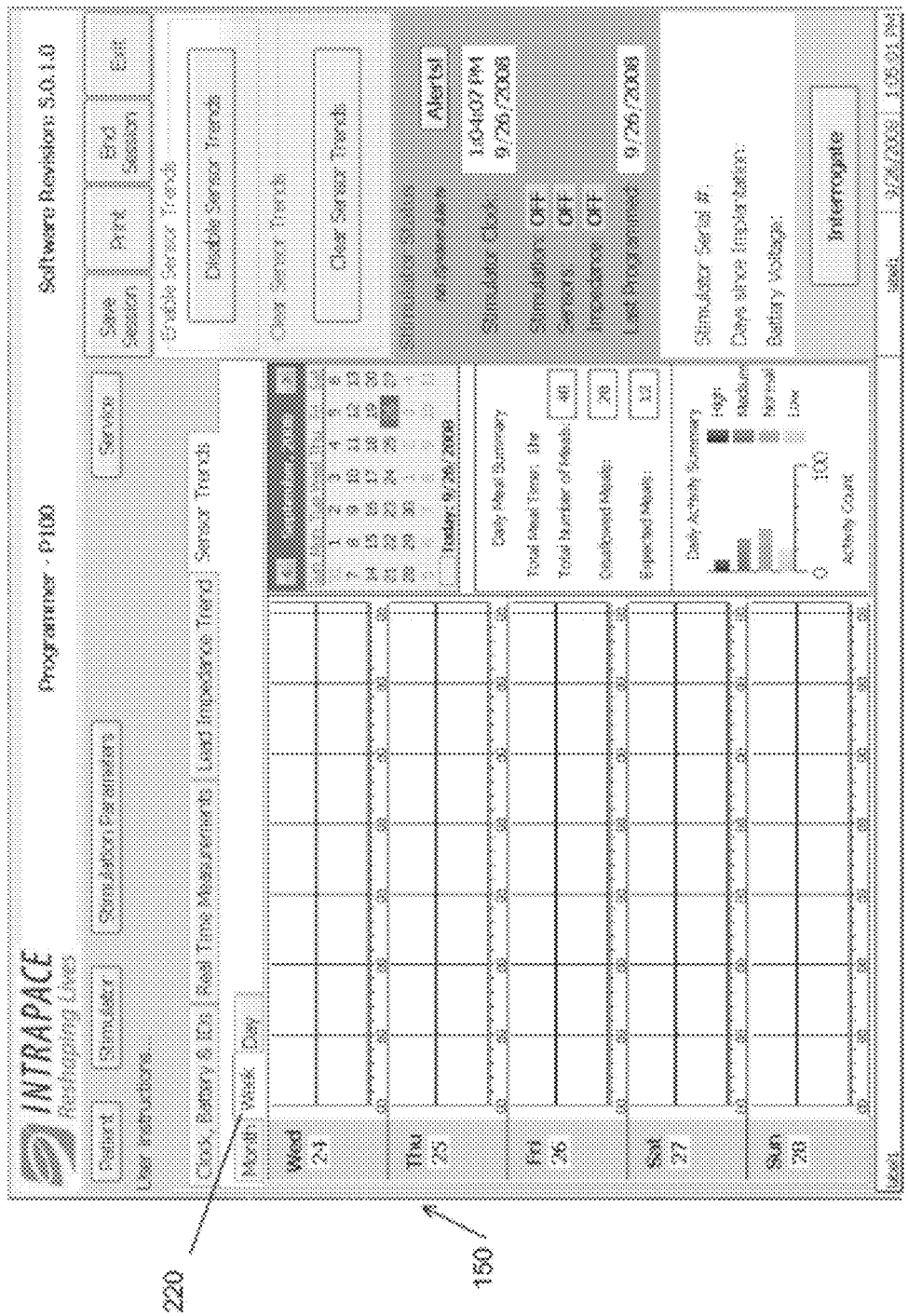

Referring to FIGS. 2A-2C, the patient web site 150 may present monthly 200, weekly 220, and/or daily 210 views. For each day shown, the following data may be presented: activity summary averages 230 (in some embodiments, these are presented in fifteen minute increments), activity summary histograms 240 (where activity may be shown grouped into four levels: daily energy expenditure, duration and intensity of exercise sessions, calories burned, and sleep quality information), consumption events 250 (i.e., eating, drinking, mixed eating and drinking), meal counts 260, therapy events 270, battery measurement 280, and/or lead impedance 290. In some embodiments, telemetry from the implanted device to a home monitor, portable device, physician's workstation, or the like with sufficient patient data for ingestion and/or activity reports encompassing thirty days of clinically relevant data may be transmitted in less than one minute. In preferred embodiments, such reports may be generated in about 45 seconds or less.

In some embodiments of the present invention, portal 150 (or another device of the system) may be adapted to accept input from other web-enabled home appliances such as electronic scales, glucose monitors and personal digital assistants (such as for keeping a patient's diet and exercise diary). Some embodiments of the present invention may also allow data collected during office visits from, for example, the implanted device 110, to be manually uploaded to the server 130 and made available to the patient and his or her coaches.

Figure 3A:
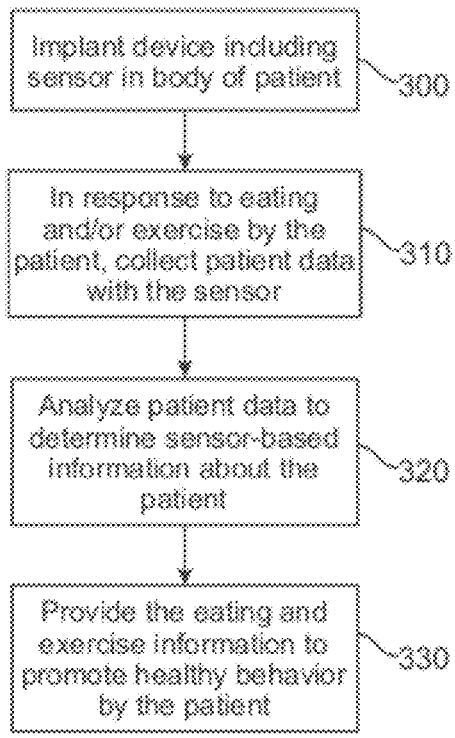
FIGS. 3A-3D illustrates treatment methods according to embodiments of the present invention.

FIG. 3A illustrates a treatment method according to an embodiment of the present invention. Initially, a device including a sensor is implanted in the body of a patient (step 300). In some embodiments, the device may be implanted in the abdomen of the patient or, preferably, in the stomach of the patient. Patient data is collected with the sensor in response to eating and/or drinking by the patient (step 310). The patient data is then analyzed to determine sensor-based information about the patient (step 320). The sensor-based information is provided to a patient and optionally his or her coaches to promote the healthy behavior of the patient (step 330).

Figure 3C:
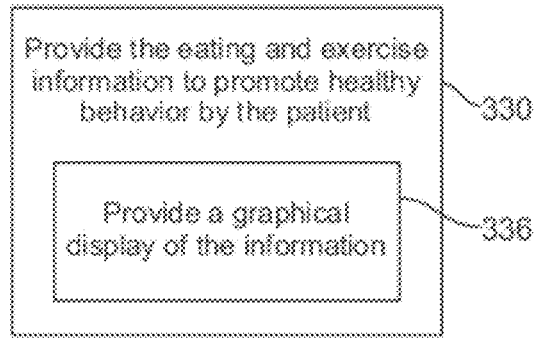
Figure 3B:
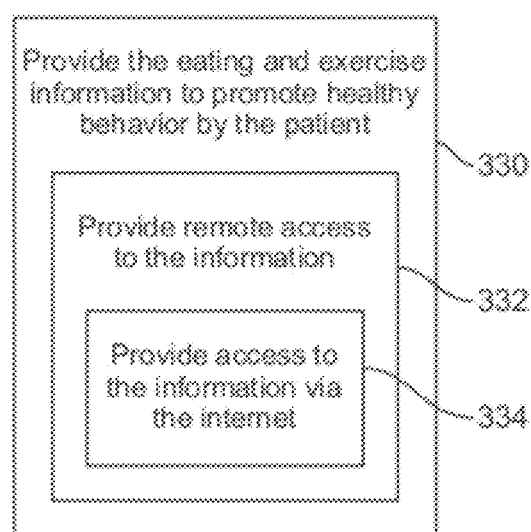
Figure 3D:
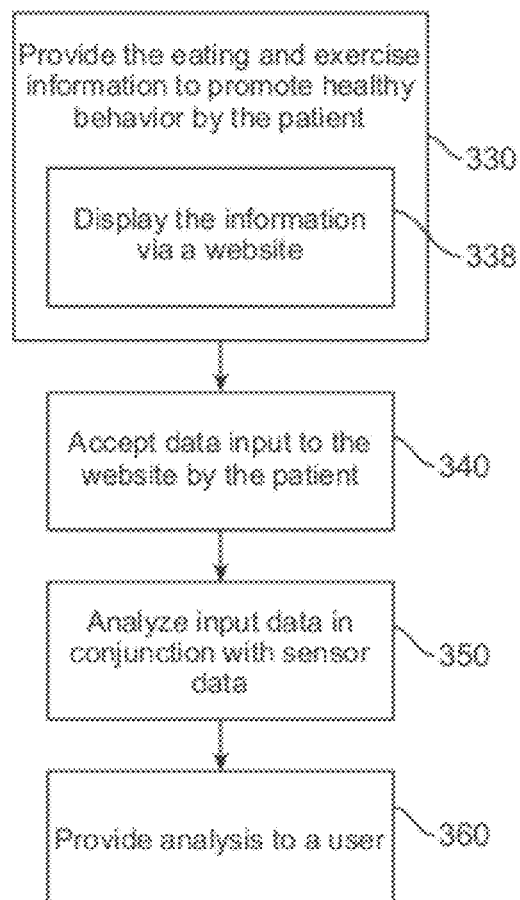

As shown in FIGS. 3B and 3C, step 330 may include providing remote access to the information (step 332), which may also include providing access to the information via the internet (step 334) and step 330 may include presenting a graphical display of the information (step 336). In some embodiments, such as illustrated in FIG. 3D, step 330 includes displaying the information via a website (step 338) and the method further includes accepting data input to the website by the patient (step 340) and analyzing the input data in conjunction with the sensor data (step 350). The resulting analysis is then provided to a user (step 360).

Figure 4A:
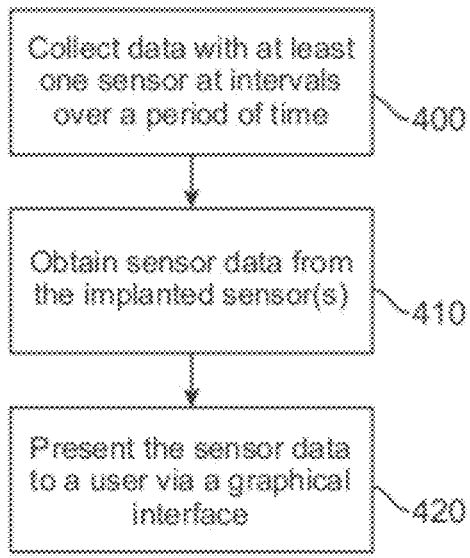
FIGS. 4A and 4B illustrate communication methods according to embodiments of the present invention.
Figure 4B:
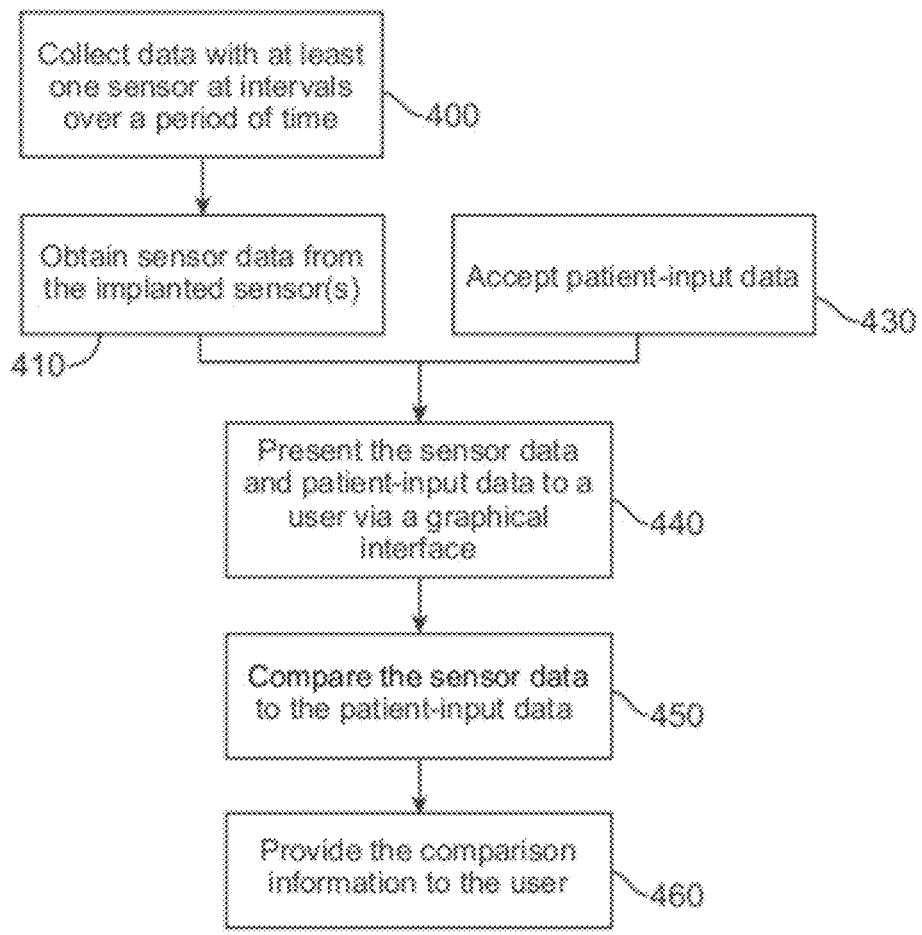

FIG. 4A illustrates a communication method according to an embodiment of the present invention. Data is collected by at least one implanted sensor at intervals over a period of time (step 400). The sensor data is obtained from the sensor(s) (step 410) and presented to a user via a graphical interface (step 420). Referring to FIG. 4B, in some embodiments, the method may include accepting patient-input data (step 430) and presenting both the sensor data and the patient-input data together (step 440). The sensor data and the patient-input data may also be compared (step 450) and the comparison information provided to the user (step 460). The sensor data may include ingestion and/or activity level information.

An exemplary method 500 for prompting a patient to enter information in response to sensor-based data is shown. Data is collected with the sensor or sensors at regular intervals over a period of time 502. The sensor data is obtained from the implanted device 110 (see FIG. 1). The sensor data may be obtained by a device associated with the patient, typically by home monitor 120 via a RF signal. In alternative embodiments, the sensor data may be obtained by a smart phone or other mobile computing and wireless communication device, or the like. The sensor data may be communicated from home monitor 120 or other device in communication with the implanted device 110 and uploaded to a server 130, or the sensor-based data may be locally processed by the home monitor. Regardless, the device sensor data is presented as a journal framework 506 to the patient, thereby prompting the patient to enter additional information regarding an ingestion event or exercise activity.

Preferably, the system will compare the sensor data to the data input by the patient 508, and will accept the patient input data 510 where the two appear to substantially align. In contrast, if the data input by the patient does not appear to be consistent with the data from the sensor, the patient may again be prompted to enter data, or a follow-up intervention may be initiated by a message to a support group member, health coach, or the supervising physician so as to increase the accuracy of reporting by the patient and/or perform diagnostic checks on their implanted device.

A comparison between the sensor data and the patient input data is provided to the user 512, and additional input data is accepted from the user 514. Once the sensor data and patient input data have converged 516, the converged data is presented to a user via a graphical interface or the like. Note that the converged data may be presented to a user different than the patient such as a support group member or physician. A number of variations are also possible, with the physician having the capability of viewing the iterations between initial entry of patient data and convergence between patient entry and the sensor data, while other support group members see only the converged data output.

Figure 6:
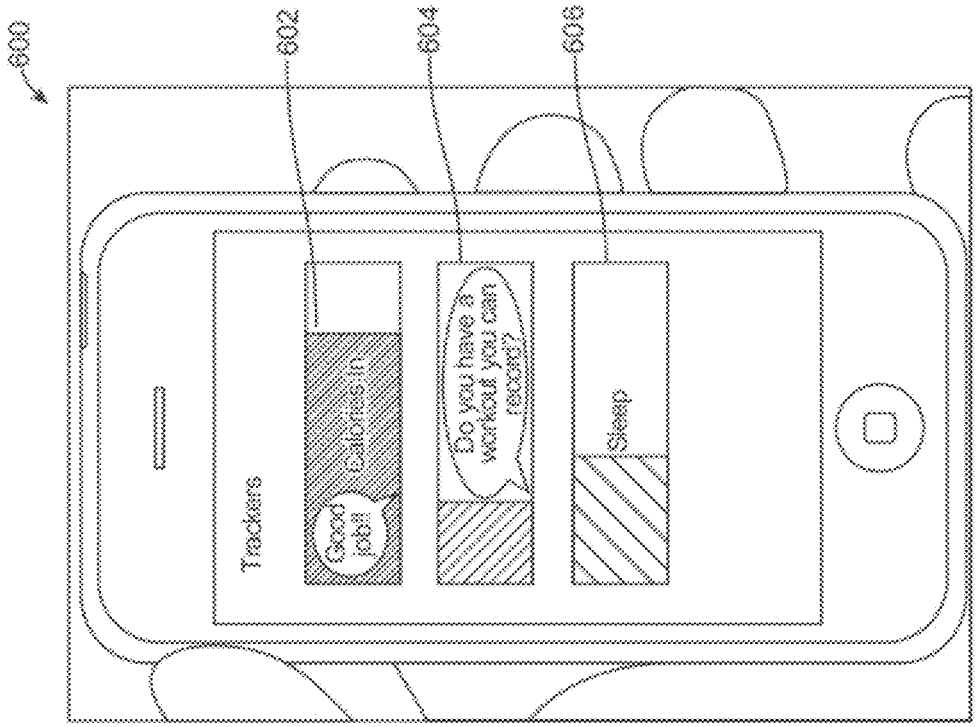
FIG. 6 illustrates message data sent to a patient via a smart phone associated with the patient so as to provide feedback on ingestion and exercise and promote healthy behavior by the patient.

Referring now to FIG. 6, an exemplary mobile device 600 associated with a patient or other group member is illustrated. The exemplary illustration shows an iPhone® smart phone commercially available from Apple Inc. Mobile device 600 has downloaded software which graphically indicates ingested calories 602 for ingestion events, energy expenditure in calories 604, and sleep quality and/or quantity 606 with the patient optionally being prompted to enter information in response to sensed data. Mobile device 600 with the software loaded therein (together with its communication capabilities) may sometimes be referred to herein as an Abiliti™ mobile device, and is generally associated with the user and owner of the mobile device 600. An Abiliti™ mobile device can communicate with the implanted device 110 using RF telemetry, directly via Bluetooth, or through a USB enabled wand. An Abiliti™ mobile device may also communicate with the implanted device via an external Bluetooth device which interacts with the implanted device using inductive or RF telemetry. An Abiliti™ mobile device can communicate with the web server 130 through various means commercially available, including 3G, 4G, or other wireless protocols.

Figure 7:
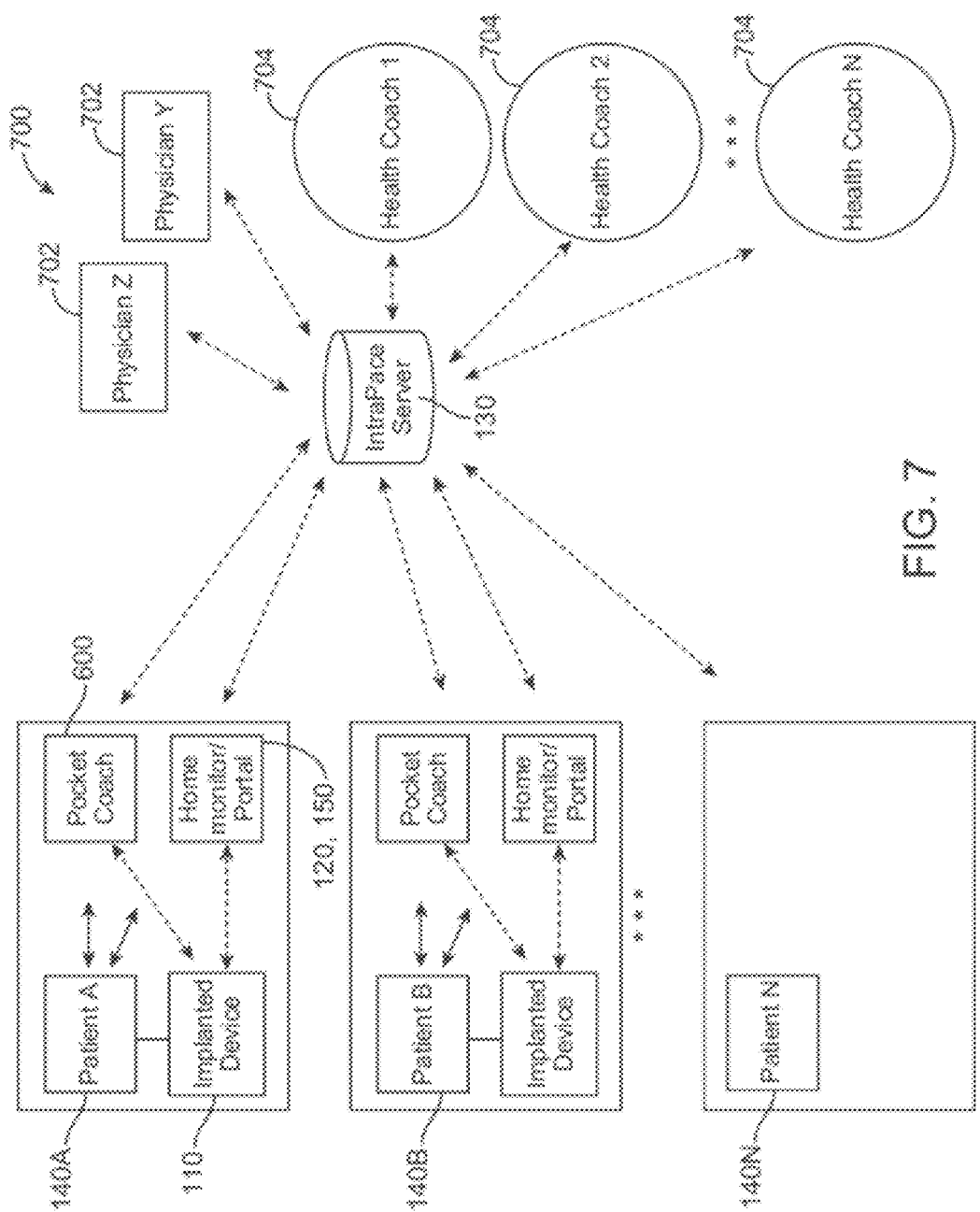
FIG. 7 illustrates an alternative embodiment of a treatment system for a group of patients belonging to a support group, in which information based on implanted sensor data can be shared with group members, at least some of the members having been granted permission to receive the information by an associated patient.

Referring now to FIG. 7, an alternative schematic illustration of a weight treatment system 700 is used to help a number of patients 140A, 140B . . . 140N to maintain a healthy lifestyle that allows them to lose significant weight. Each patient has an associated implanted device 110. Each patient will typically also have at least one associated device, such as a mobile device 600, a home monitor 120 (which may optionally comprise or interface with a desktop computer through which the patient can access portal 150), a Notebook computer, or the like. Implanted device 110 of each patient will communicate via wireless telemetry with the device 120, 600 associated with that patient, and the device 120, 600 also communicates with server or centralized data collection mechanism 130.

Along with a group of patients, a number of physicians 702 may also have associated devices (desktop or Notebook computers, mobile devices such as Smart phones or emailers, or the like) that are associated with that particular physician. Note that the associated devices may be associated to the patient, physician, or other group member by downloading software from server or centralized data collection mechanism 130, entering a password, and the like, so that the device or devices associated with the particular user may change over time. Regardless, each physician 702 will typically have access to information based on sensor data from one or more specific patients. Specifically, for a patient A being treated by physician Z, a sensor of implanted device 110 will generate sensor signals in response to an eating event and/or an exercise activity of patient A. The sensor data may be recorded and/or processed at least in part in the circuitry 116 of implanted device 110 (see FIG. 1). Sensor-based data or information is transferred wirelessly from implanted device 110 to the device associated with patient A (such as the mobile device 600 or home monitor 120), and information regarding ingestion and/or exercise of the patient that has been generated using the sensor signals from one or more sensors can then be uploaded to server or centralized data collection mechanism 130.

Server or centralized data collection mechanism 130 may transmit to physician Z message data, with the message data typically being sent to a computer, smart phone, or other device associated with physician Z. The message data is generated by server or centralized data collection mechanism 130 using the uploaded sensor-based information, with the message presented to physician Z, typically including data suitable for the physician's need in supervising treatment of patient A. For example, longer term trend data regarding the patient's ingestion, exercise activities, weight, and the like may be presented to physician Z so as to facilitate identification of patterns in the patient's eating and exercise. A web portal 150 associated with physician Z may also provide the physician with the capability of comparing different patients (such as patient A and patient B) or groups of patients by overlying or otherwise comparing graphs of weight loss, ingestion, activity endpoints, or the like. This may allow the physician to identify additional treatment parameters for particular subpopulations. compare different efficacies of differing types of support groups or coaching, or the like. The portal 150 associated with a physician 702 may also facilitate reprogramming of a therapy for the patients of that physician, including tools that correlate device programming parameters with therapy efficacy. Hence, the physician may be able to modify an implanted device 110 of a particular patient so as to tailor ingestion-inhibiting stimulation for that patient, may be able to modify aspects of the relationships between patients or other users of system 700, and the like. As a physician 702 may be involved in bringing a patient 140 into the treatment regime of system 700, patients may not need to grant permission to their physicians for the physician to obtain access to patient data. In other embodiments, the patient may have the ability to grant permission to a physician so as to include the physician in some or all types of data available via network 700 regarding that patient.

In an alternative embodiment, the implanted device could administer adaptive therapy, continually adjusting meal sessions. For example, the device could detect the mealtimes and then administer the therapy accordingly, by adapting the schedule in the device. In an alternative embodiment, a home computer may be used to re-program the device. In yet another alternative embodiment, a user may select the therapy to be administered from a set of pre-programmed options. For example, the pre-programmed options may include a meal session schedule appropriate for the weekend, and one appropriate for the week days. Or in the case of an employee with different work shifts there may be a meal session schedule appropriate for a night shift and a day shift. The doctor would specify the parameters for each pre-programmed option in consultation with the patient, and then the patient may select from the pre-programmed options when needed from home.

In addition to facilitating patient/physician communication, network system 700 may also facilitate weight loss of patients through the participation of additional health coaches 704. In some embodiments, a particular health coach may be assigned to a patient by the patient's physician 702. In other embodiments, the health coach for a particular patient will be invited to join a group for that patient, with the patient granting permission to the health coach to access some or all of the patient's data (including sensor-based data). Patients 140 may grant varying levels of permission and access to data to health coaches 704, and patient A 140A may also grant access to the data of patient A. Similarly, patient B may (but need not necessarily) grant patient A access to sensor-based data from the implanted sensor of patient B. Hence, some (though not necessarily all) of the support group members for a patient may include another patient having an implant. Where patients grant permission for access to each other, the resulting support group may deepen the relationship between the patients and efficacy of the network at assisting weight loss.

The message data transmitted from server or centralized data collection mechanism 130 to the group members of a particular patient (including health coaches, other patients in the group, and the like) may include diary or journal entries by the patient, sensed eating events and/or exercise activities, text messages from the patient or other group members, and the like. Information regarding other groups in which one or more of the group members is included may also be available. Hence, a number of tools available to social networking systems may be employed. Messages may be presented to the health coach 704 when (and in response to) the health coach logs in to the system, or message data may be sent to prompt messages when the health coach is off-line via text messages, voicemail, etc.

Along with sensor-based events triggering sending of messages, the system may also send messages or reminders to the patient or group that are time based. As an example, the server (or a device associated with a group member) might send a reminder at the end of the work week with suggested activities and menu items for the weekend. Similarly, each day an inspirational message could be sent to some or all of the members of the group. In some embodiments, time-based and/or sensor-triggered messages may be sent by the system to remind the patient to complete other tasks e.g. check their blood pressure, weigh in, exercise, etc. These messages could be in support of collecting information from other networked appliances like a digital scale, blood pressure cuff, and/or glucose meter.

Figure 8:
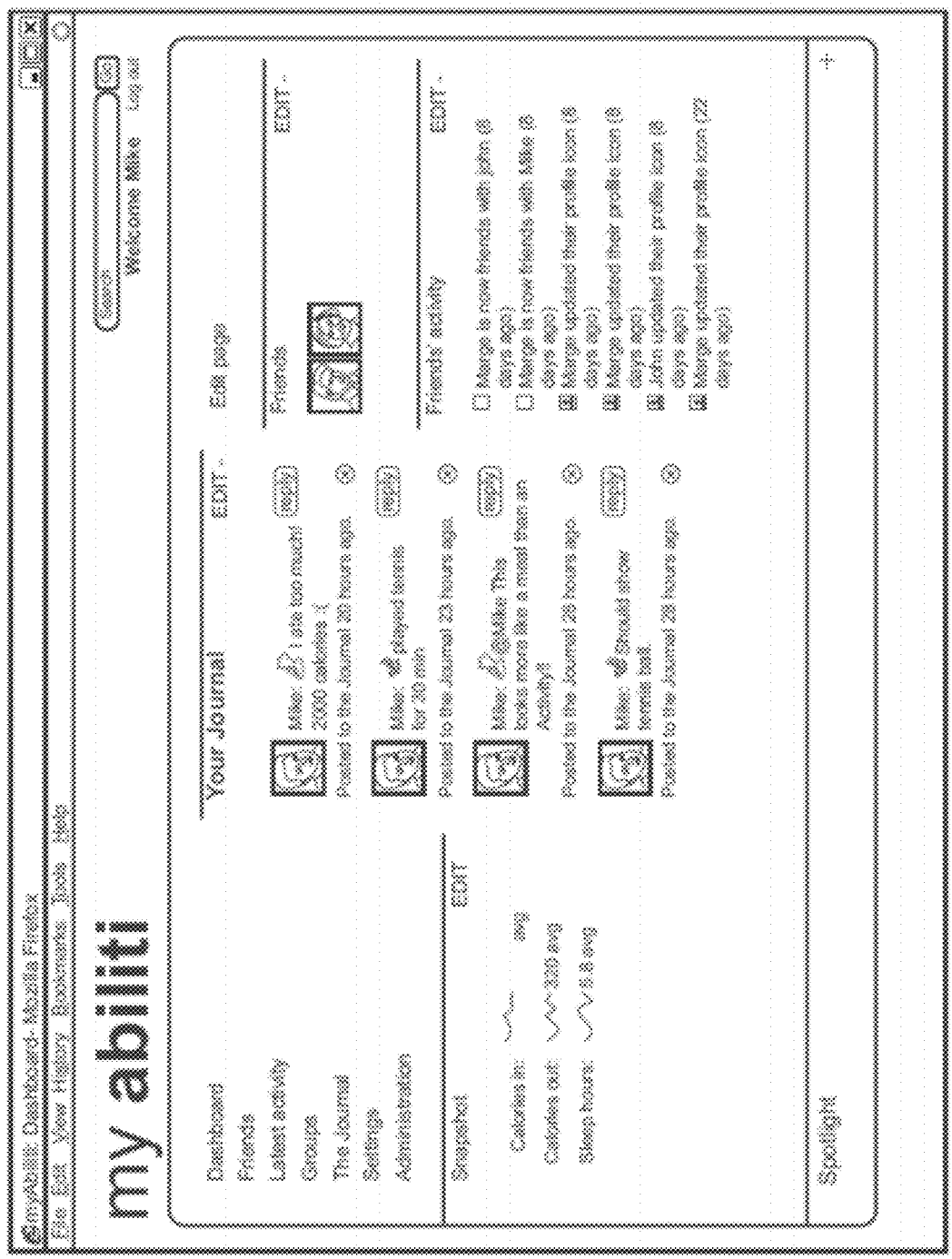
Figure 9:
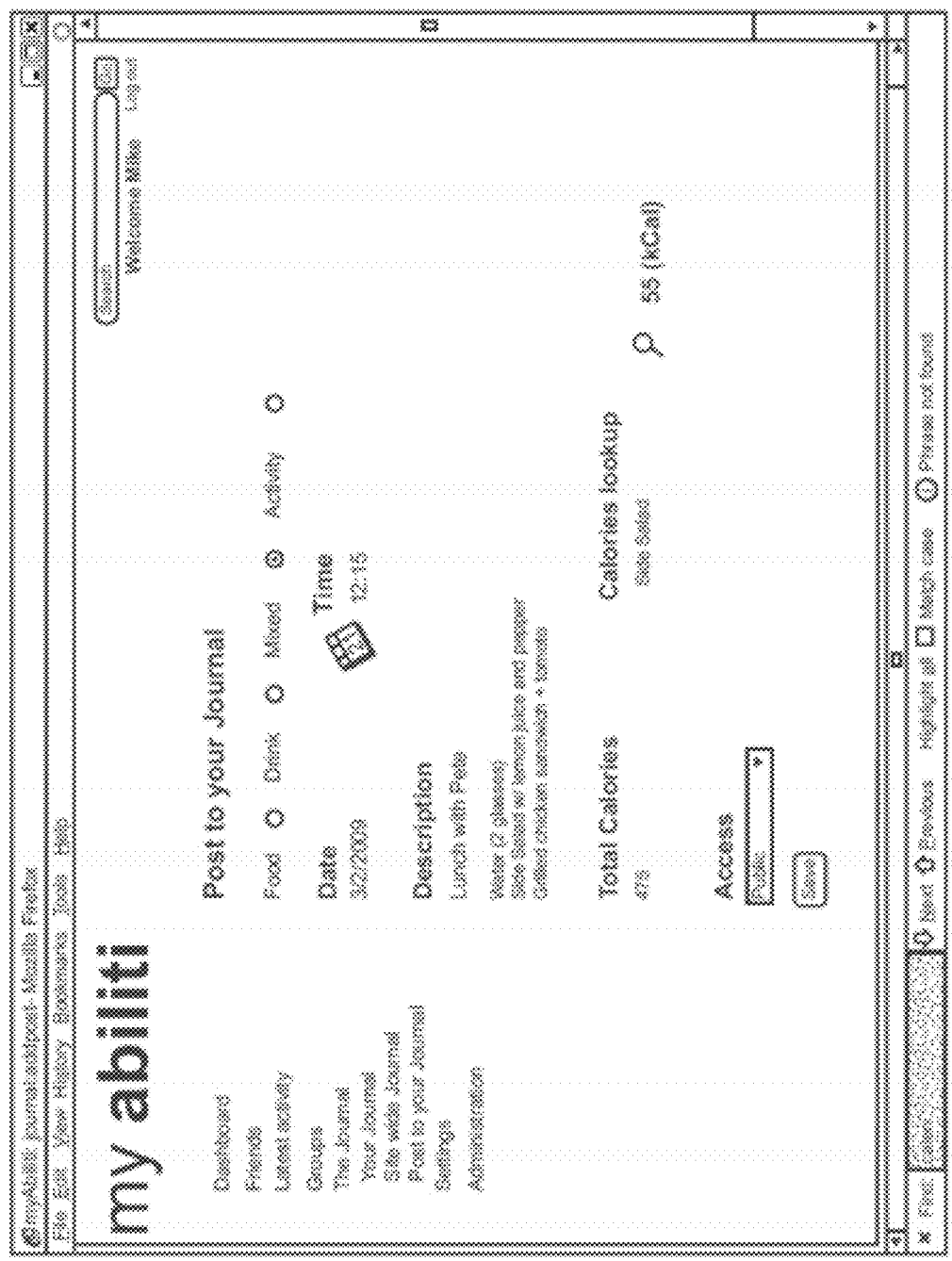
FIG. 9 is a screen shot showing a page which prompts a patient to provide information regarding ingestion in response to sensor-based information.
Figure 10:
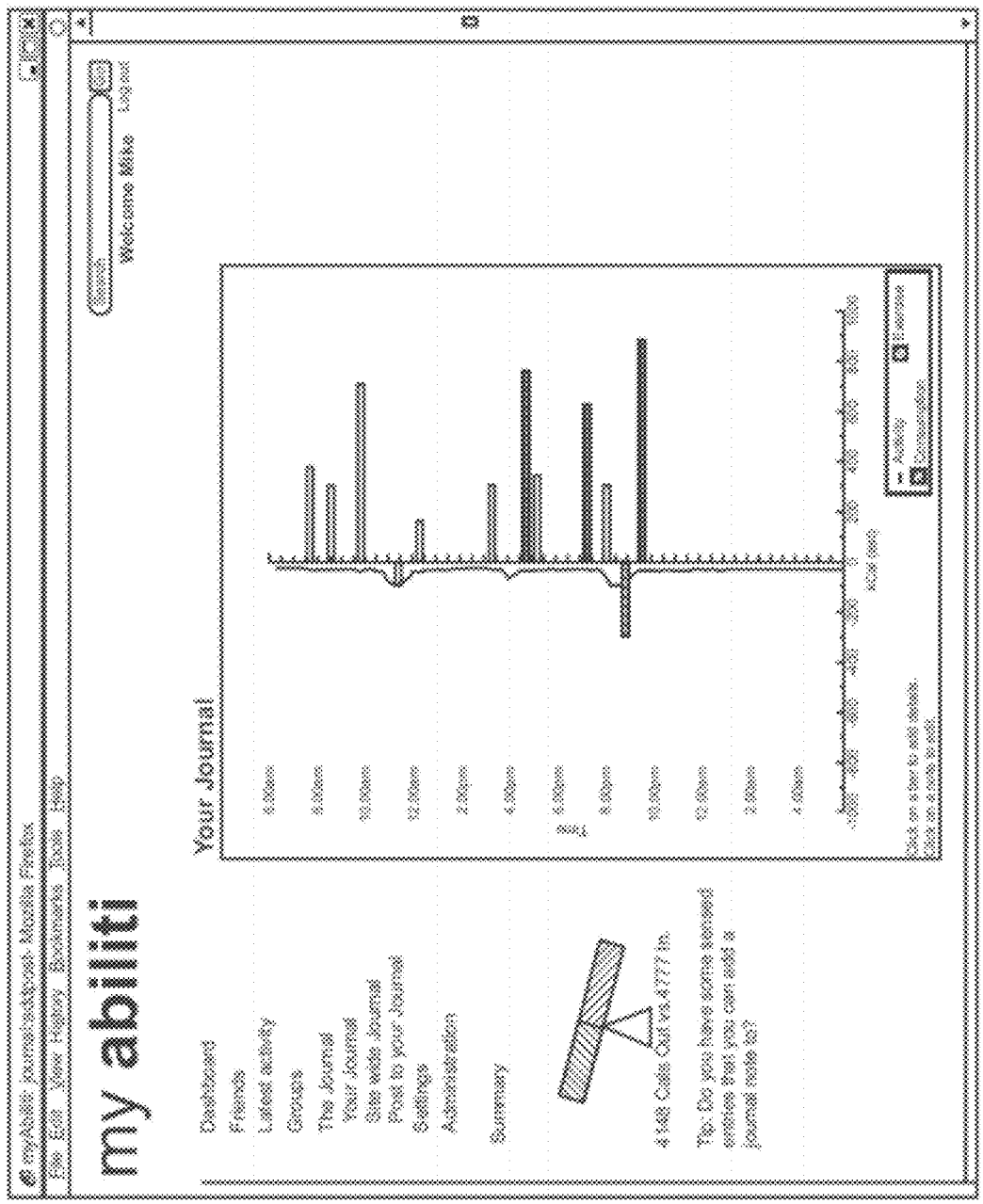
FIG. 10 is a screen shot showing summary information regarding ingestion events and activity levels for a patient.

FIGS. 8, 9, and 10 illustrate exemplary pages included in portal 150, with the screen shot of FIG. 8 showing a dashboard page that provides a snapshot of recent sensor-based information and a listing of recent journal or diary entries. Access is provided to a "Friends" page on which the patient can modify the group by granting access to additional individuals so as to join the group, limit or expand permission for accessing data to one or more of the existing group members, or eliminate certain individuals from the group that supports (and has access the sensor data of) the patient. A listing of the activity of the group members in updating their profiles, joining other groups or extending invitations to other individuals to join their groups, and the like, may also be provided on the dashboard.

Figure 5:
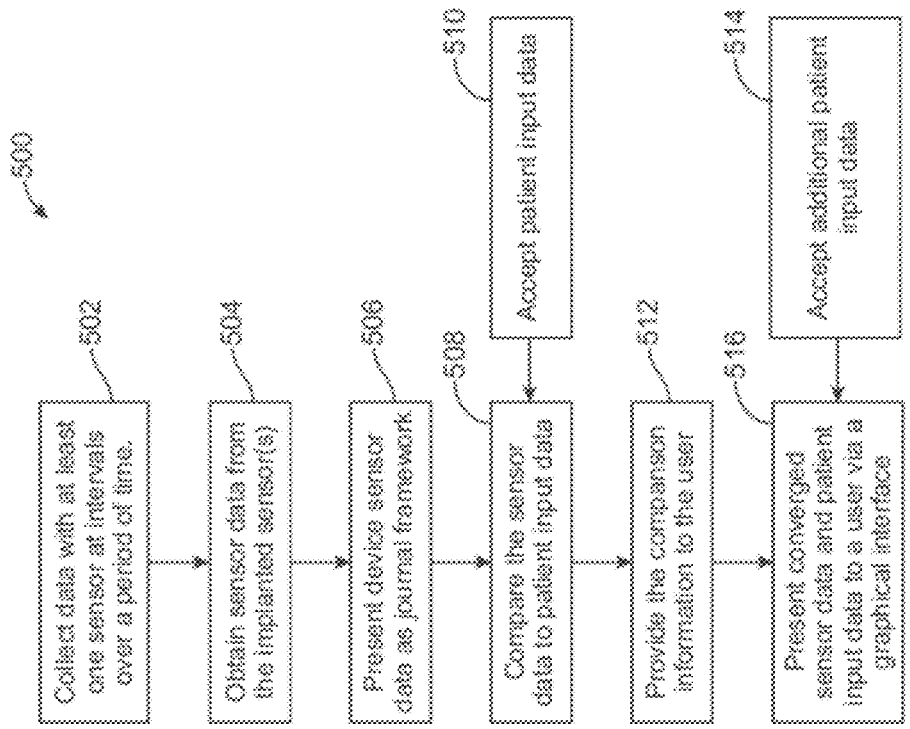
FIG. 5 illustrates a method for prompting a patient having an implanted sensor to enter additional information regarding sensed ingestion and/or exercise.

FIG. 9 shows a journal entry page which allows the patient to enter information regarding a meal or exercise activity, with the journal entry page optionally having at least a portion of the data supplied via sensor-based information. In some embodiments, a prompt to fill out the journal page may be sent to the patient in response to sensor-based information. If a patient attempts to enter data which is inconsistent with the sensor-based information, the system may prompt the patient for correction of the data as indicated above regarding FIG. 5.

FIG. 10 is a screen shot illustrating a journal summary showing ingestion and exercise activities, with a graphical indication in the form of a balance showing whether the ingestion calories exceed energy expenditure (in calories) (so that weight may be increased) by the patient's behavior over a recent increment of time (such as over the last day, two days, week, or month).

Table 1 below shows use cases associated with an embodiment of mobile device 600 so as to allow the patient to have access to information and enter data via a Smart phone, emailer, or other portable device.

TABLE I

1 Patient
  1.1 Use food calculator
  1.2 Read educational item
  1.3 Record meal
  1.4 Record Activity/Exercise
  1.5 Share personal status
    Personal status is a brief update shared by the patient. This can include the patient's mood, their current activity, what they are thinking about, etc.
  1.6 Initiate retrieval of device data
2 System
  2.1 Send daily message
    The system shall send a daily inspirational message to subscribed patients.
  2.2 Upload data to server
  2.3 Upload data to server Data can include data retrieved from the implanted device as well as patient entered data.

Table II is a listing of use cases for portal 150, showing some of the capabilities of the portal at communicating information or messages to the patient, and for accepting data entered by the patient or other system user.

TABLE

PROCEDURE 1.0 Patient
  1.1 Patient registers with portal
  1.2 Record meal
  1.3 Record Activity/Exercise
  1.4 Record weight
  1.5 Share personal status
    Personal status is a brief update shared by the patient. This can include the patient's mood, their current activity, what they are thinking about, etc.
  1.6 Upload data from external appliance
  1.7 Use food calculator
  1.8 Record health status
  1.9 Create Friend relationship
  1.10 Record goals
  1.11 Modify permissions
  1.12 Invite Supporter to community
    The primary method for Supporters to join community is by an invitation by a Patient.
  1.13 Record sleep information
2.0 Clinician
  2.1 Clinician registers with portal
  2.2 Enter plan for patient
  2.3 Upload device data
    Data retrieved through a Programmer may be uploaded through the portal.
  2.4 View historical data
    The Clinicians will see an extended set of data beyond the standard "View historical data" use case. Examples: i.e. longer term trending of data, temporal patterns for the patients sleeping and eating, the ability to compare their patients progress by overlaying graphs of weight loss or activity endpoints, provide tools for correlating device programming with efficacy.
  2.5 View historical data for Group
  2.6 View summary data for Group
3.0 Common
  3.1 Groups
    Groups are collections of users. Groups can be formed around many purposes: a topic, a geographic location, a shared coach or clinician, a body type, or goals.
    3.1.1 Join group
    3.1.2 View group messages
    3.1.3 Compose group message
    3.1.4 Create Group
    3.1.5 Invite to Group
  3.2 Forums
    Forums are threaded conversations, typically about a general topic. Groups also have group messages, but their distribution is restricted to the members of the group. The write privilege in forums shall only be granted to patients and clinicians.
    3.2.1 Add Forum message
    3.2.2 Reply to Forum message
    3.2.3 Remove Forum message
    3.2.4 Search Forum
  3.3 Access web portal
    3.3.1 Using a web browser, the user navigates to the web portal site.
    3.3.2 System displays a welcome screen including text input areas for user name and password.
    3.3.3 User enters correct user name and password.
    3.3.4 System displays the user's home screen.
  3.4 Send personal message
  3.5 Participate in Chat
  3.6 Suggest educational information/link
  3.7 Read educational item
  3.8 Report abuse
    Allows any user the ability to report inappropriate behavior to the System Administrator.
  3.9 View historical data
  3.10 Edit user profile
    The user profile contains administrative items (eg. user name, password), portal items (eg. avatar, signature line), and shared user information (eg. location, gender, goals, etc.)
  3.11 View summary data
    View recent data in a summary format. This data will include sensor data as well as user recorded information (eg. meals and activities).

-continued

| PROCEDURE |
|---|
| 4.0 System |
| Use cases performed by the IntraPace System (typically server based tasks). |
| 4.1 Send realtime coaching message to Patient |
| 4.2 Receive data logs |
| 4.3 Send alert to Clinician |
| Alerts can be configured to be sent based on Patient events, typically achieving or missing a goal. |
| 5.0 Supporter |
| Supporters are individuals typically invited by Patients to participate in the community. |
| 5.1 Supporter registers with portal |

A variety of alternative and/or additional sensors might be included in the systems described above. For example, the systems may take advantage of global positioning system sensors (GPS) or other position sensing technology to increase specificity of feedback provided to one or more patients. GPS position information may be available in from GPS sensors included in many smart phones or from a separate GPS unit, and can identifying the location and movements of a patient. As an example the system determines the patient is located at a certain restaurant, the server (or another group member) could send a message configured to support the patient in that environment, to encourage the patient to order from among a selection of healthy options available at that restaurant (optionally as identified via an Internet menu), give healthy food options, connect the patient to user ratings, etc. An alternative embodiment comprises using credit card payments to identify the patient's presence in a food store or restaurant and then providing the patient with the same type of information as with the GPS. If the system determines from the patient's position that the patient was hiking along a hiking trail the server might send a message with encouragement for the effort, and/or a message showing an improvement in the speed, distance, as compared to prior hikes. Uploading of position and/or movement tracking will also allow more detailed analysis of the level of your energy expenditure, including derivations of speed, distance and (using elevation information from the internet) grade information from the GPS signals.

Figure 11:
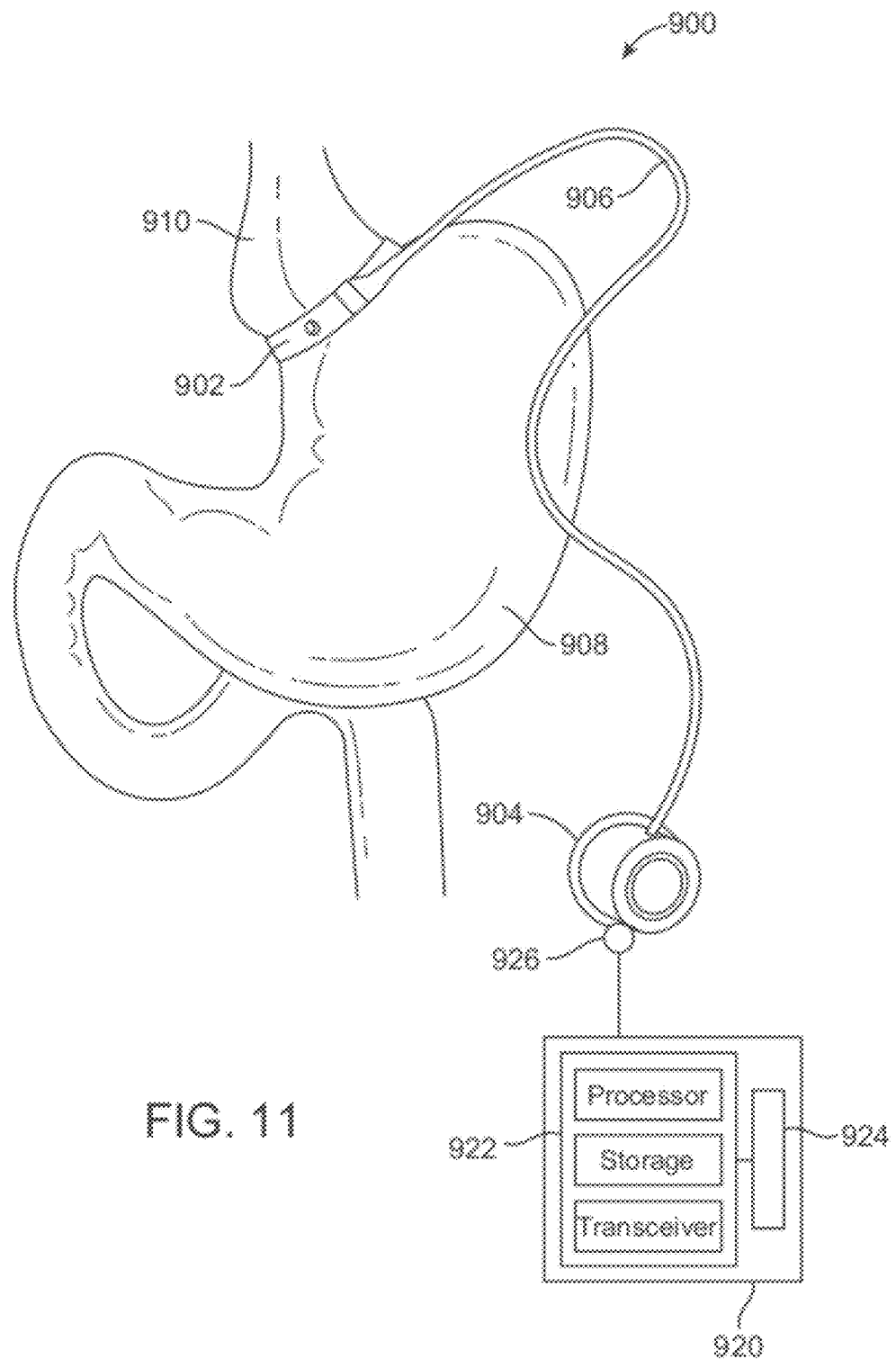
FIG. 11 schematically illustrates an alternative implanted system including a gastric band for gastrointestinal constriction and a sensor for detecting ingestion.

Referring now to FIG. 11, an alternative gastric band implant 900 is shown. This embodiment includes a gastric band 902 having a fluid-filled cuff coupled to an implanted port 904 via a fluid conduit 906. The gastrointestinal constriction provided by gastric band 902 can be varied by injecting or removing fluid from port 902 using a syringe. Along with mechanically constricting gastrointestinal flow, system 900 includes a housing 920 with circuitry 922 and a battery 924 to wirelessly transmit signals generated in response to one or more sensors 926. Note that housing 920 may optionally be incorporated into port 904.

Optionally, system 900 may sense ingestion using signals from a pressure sensor 926 coupled to the cuff inflation fluid, with the pressure sensor optionally being mounted in fluid communication with port 904. Pressure transients in the cuff inflation fluid caused by the distension of food passing through band 902 can be processed and transmitted using circuitry 922 to a home monitor, portable device, or the like. In some embodiments, an electrical conduit extends from a temperature sensor within the stomach, through a transgastric port, and to circuitry 922. This electrical conduit or lead could, but need not have any stimulating electrodes. Suitable trans-gastric temperature sensing probes and ingestion analysis may be coupled to this or another lead, with suitable components described in (or may be modified from those described in) U.S. Provisional Patent Application No. 61/122, 315, filed on Dec. 12, 2008, the full disclosure of which is incorporated herein by reference. Still further alternatives are also possible, including gastric balloon systems having sensors and telemetry circuitry suitable for implantation in the stomach cavity, endoscopically deployed stimulation systems having sensors and telemetry circuitry suitable for implantation in the stomach cavity, and the like.

While exemplary embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A system for providing feedback to treat an obese patient comprising:
   an implantable sensor adapted to be coupled with the stomach of the patient, the sensor configured to sense patient data related to a food ingestion event;
   an implanted wireless transmitter coupled to the sensor;
   a wireless portable device comprising a processor, a storage medium, and transmitting/receiving circuitry, the wireless transmitter configured to transmit sensor-based patient data related to the food ingestion event to the device when the patient is within a distance less than about 30 feet from the device;
   a GPS receiver configured to determine position signals indicating patient location; and
   a remote server, the server comprising a tangible medium embodying machine-readable instructions for analyzing the sensor-based patient data related to the food ingestion event received from the device and the position signals from the GPS receiver and for, in response thereto, communicating analysis results to the patient or at least one other user via at least one of an email, a text message, a phone call, or a web page to reinforce healthy eating behavior of the patient;
   wherein the device is in communication with the sensor via the transmitting/receiving circuitry and with the server, the device configured to receive patient sensor-based patient data related to the food ingestion event from the sensor and transmit the sensor-based patient data and the position signals to the server;
   wherein the server is configured to communicate the analysis results to encourage healthy eating behavior within fifteen minutes after receiving the sensor-based patient data related to the food ingestion event and the position signals from the GPS receiver indicating patient location.

2. The system of claim 1, wherein the wireless portable device comprises a cellular telephone, a smart phone, a personal digital assistant, a handheld computer, or a notebook computer.

3. The system of claim 1, wherein the analysis results include a comparison of sensor-based performance with patient goals.

4. The system of claim 1, wherein a server determination that the patient location is in a restaurant or a food store induced the server to send a message to the patient encouraging healthy eating behavior, within fifteen minutes of receipt of position signals by the server.

5. The system of claim 1, wherein a server determination that the patient location is in a sports or outdoor recreation location induces the server to send a message to the patient encouraging healthy exercise activity, within fifteen minutes of receipt of position signals by the server.

6. The system of claim 1, further comprising patient stimulation circuitry wirelessly coupled to the device and/or coupled to the sensor, wherein the circuitry is adapted to be implanted in the patient and includes at least one electrode, the electrode(s) coupled to the sensor by a processor of the circuitry so that the processor processes the data and delivers ingestion altering signals to the patient via the electrode(s).

7. The system of claim 1, wherein the device is also configured to receive data from at least one of an electronic scale, a glucose monitor, blood pressure cuff, a telephone, an image capture device or a personal digital assistant.

* * * * *